US011266362B2

(12) United States Patent
Fukuzaki et al.

(10) Patent No.: US 11,266,362 B2
(45) Date of Patent: Mar. 8, 2022

(54) X-RAY DETECTION UNIT FOR WHEELCHAIR, AND X-RAY DIAGNOSTIC APPARATUS

(71) Applicant: Canon Medical Systems Corporation, Otawara (JP)

(72) Inventors: Takehiro Fukuzaki, Utsunomiya (JP); Masaharu Soya, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 16/890,120

(22) Filed: Jun. 2, 2020

(65) Prior Publication Data

US 2020/0390408 A1 Dec. 17, 2020

(30) Foreign Application Priority Data

Jun. 13, 2019 (JP) .............................. JP2019-110493

(51) Int. Cl.
*A61B 6/00* (2006.01)
*A61B 6/04* (2006.01)

(52) U.S. Cl.
CPC .......... *A61B 6/4208* (2013.01); *A61B 6/0478* (2013.01); *A61B 6/4429* (2013.01); *A61B 6/5205* (2013.01); *A61B 2562/0247* (2013.01)

(58) Field of Classification Search
CPC ... A61B 6/4208; A61B 6/0478; A61B 6/5205; A61B 6/4429; A61B 6/44
See application file for complete search history.

(56) References Cited

U.S. PATENT DOCUMENTS

| 4,589,124 A * | 5/1986 | Ruiz .................... G03B 42/025 |
| | | 280/304.1 |
| 2012/0051510 A1* | 3/2012 | Ohta ...................... A61B 6/542 |
| | | 378/62 |
| 2016/0089094 A1* | 3/2016 | Kawamura .............. A61B 6/44 |
| | | 378/62 |

FOREIGN PATENT DOCUMENTS

| JP | 44-22397 | 9/1969 |
| JP | 56-50523 | 8/1979 |
| JP | H08243090 A * | 9/1996 |

* cited by examiner

*Primary Examiner* — Michael C Bryant
(74) *Attorney, Agent, or Firm* — Oblon, McClelland, Maier & Neustadt, L.L.P.

(57) ABSTRACT

According to one embodiment, an X-ray detection unit for a wheelchair includes a container and an attachment portion coupled with the container. The container is configured to contain a flat X-ray detector. The attachment portion is configured to be detachably mounted to a part of the wheelchair in which a subject is seated, so that a detection plane of the X-ray detector in the container faces the subject.

13 Claims, 19 Drawing Sheets

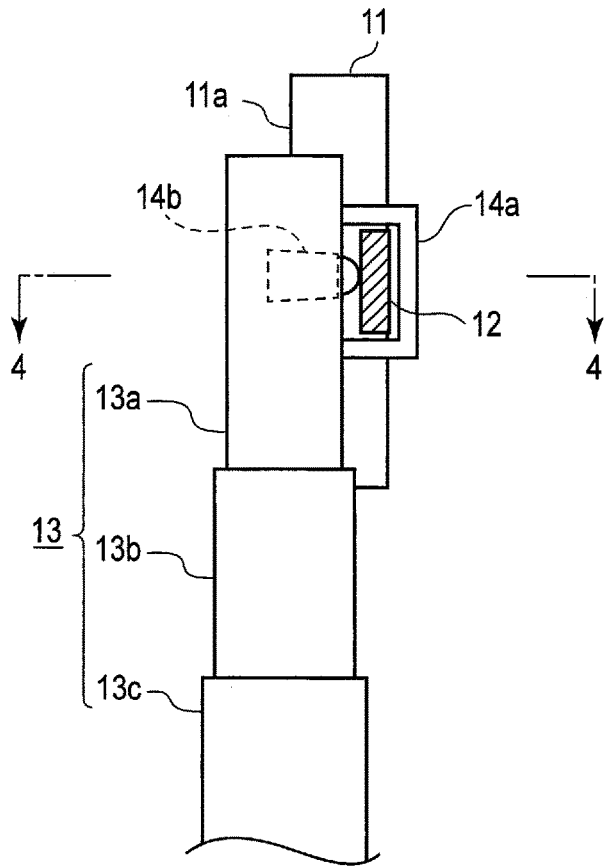
F I G. 3
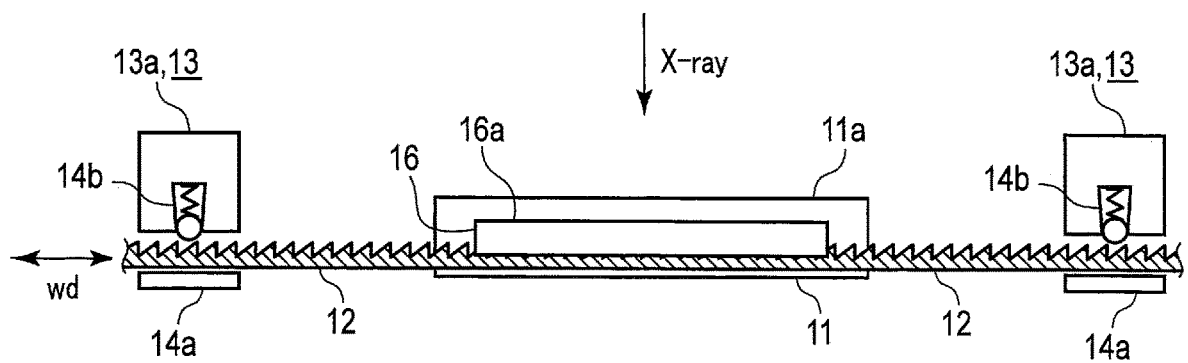
F I G. 4

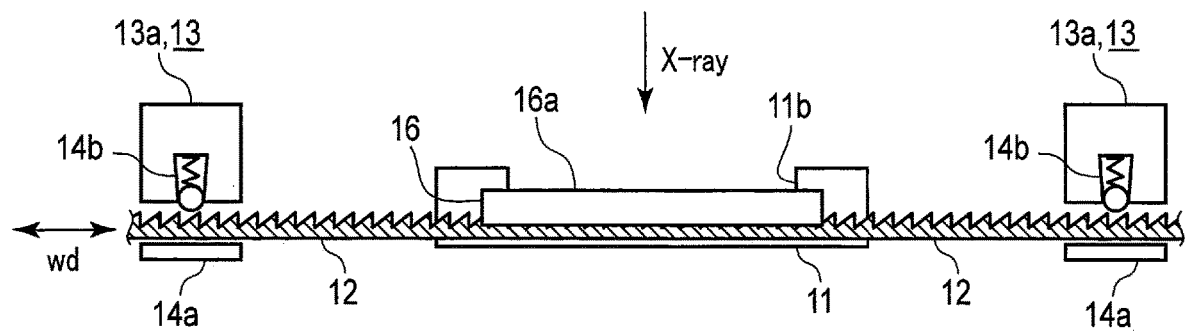
F I G. 5
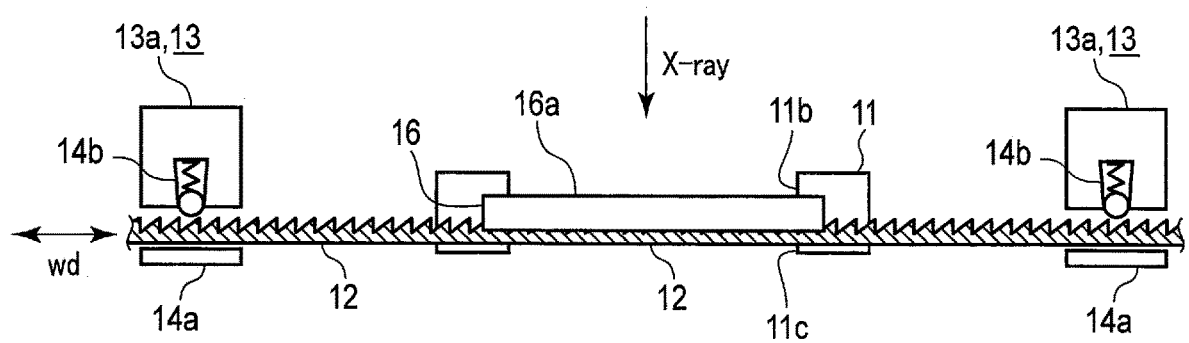
F I G. 6

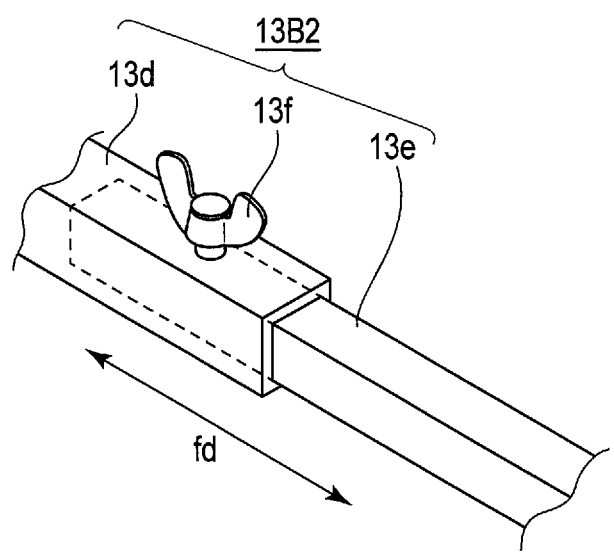
F I G. 11

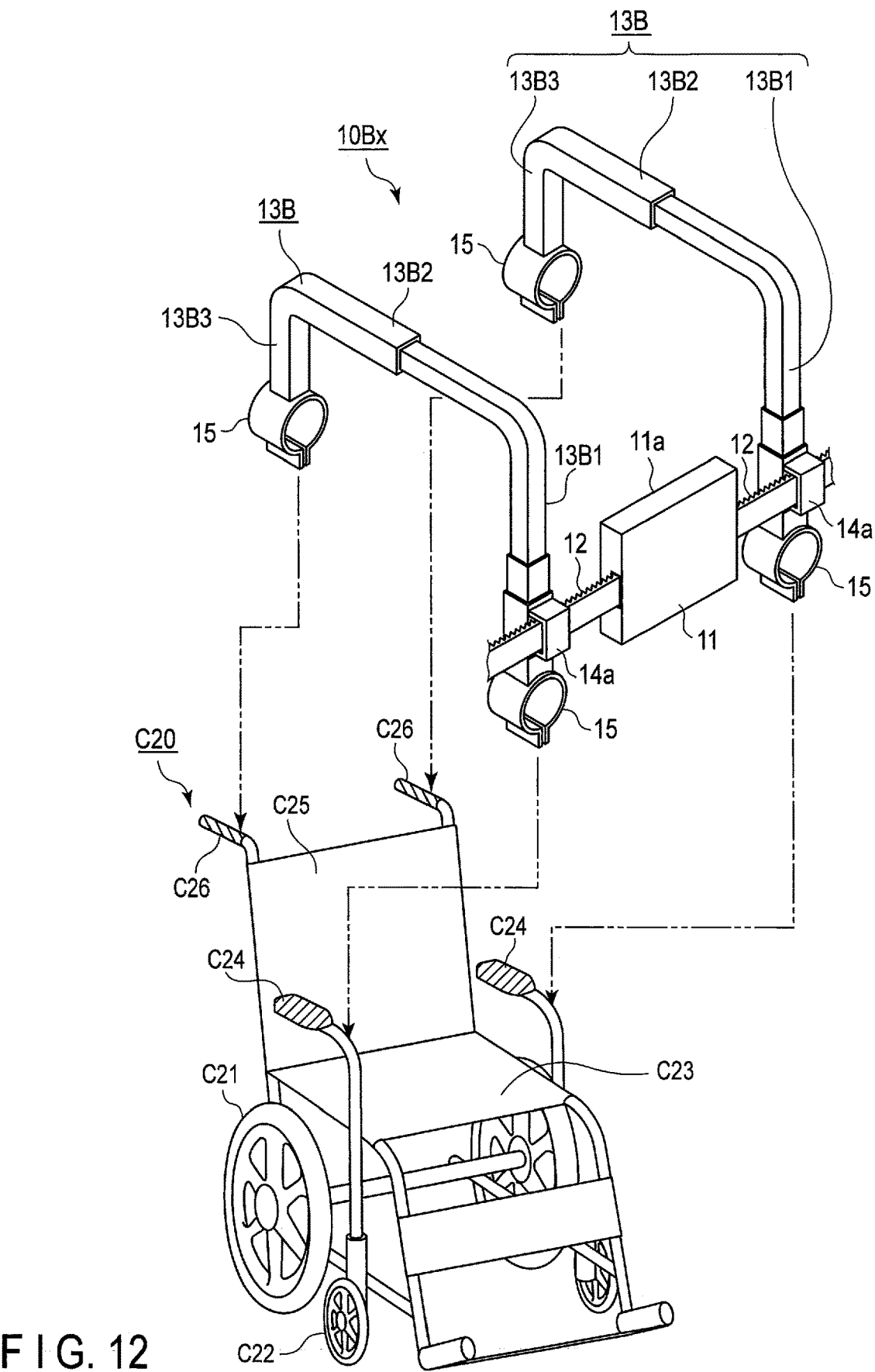
F I G. 12

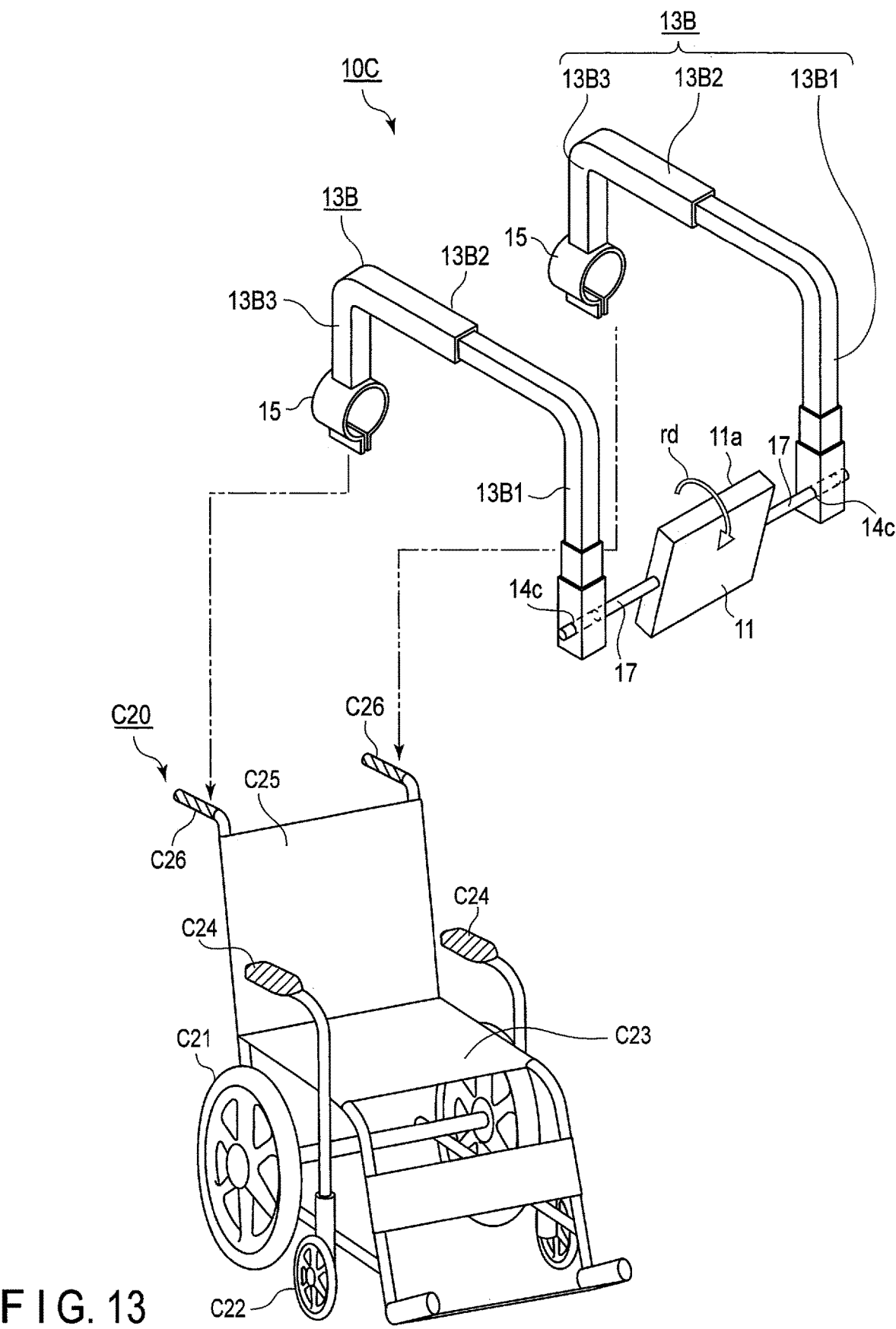
F I G. 13

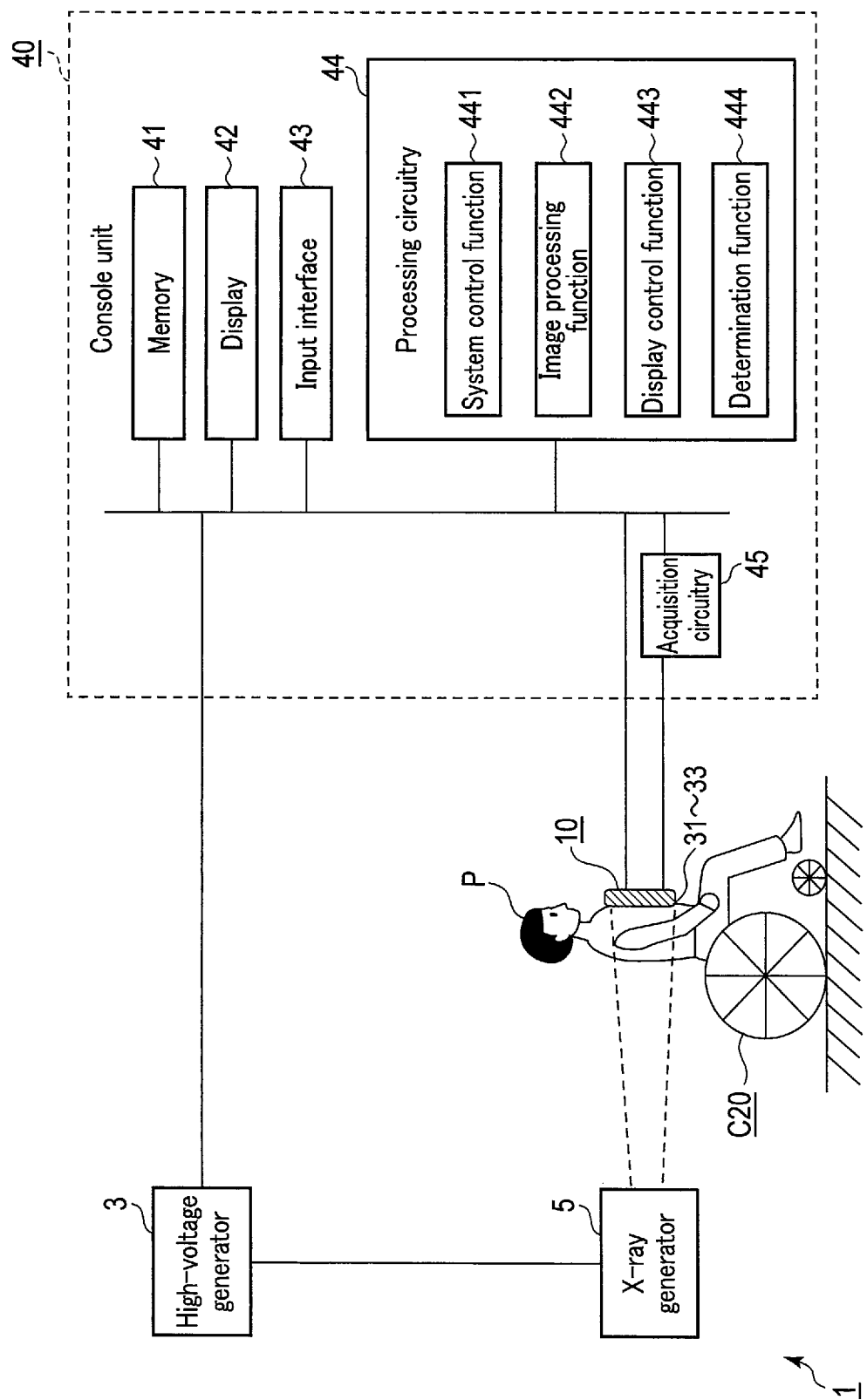
F I G. 15

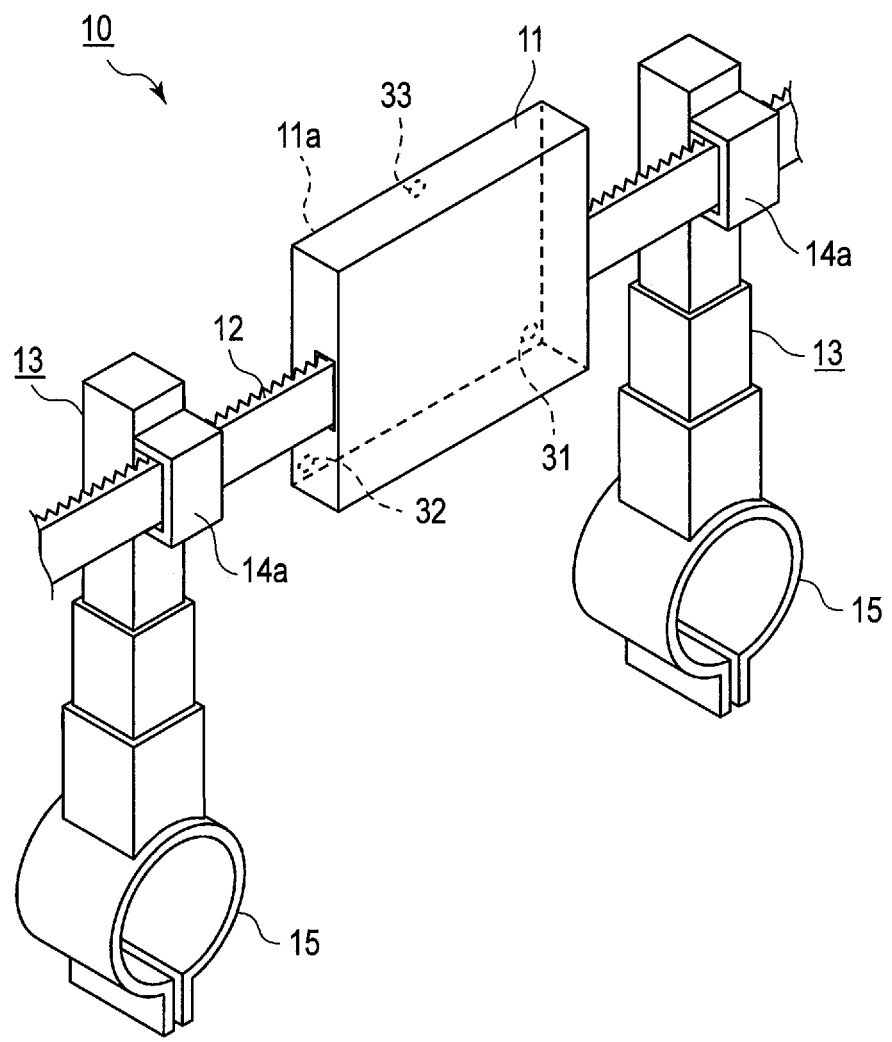
F I G. 16

X-RAY DETECTION UNIT FOR WHEELCHAIR, AND X-RAY DIAGNOSTIC APPARATUS

CROSS-REFERENCE TO RELATED APPLICATIONS

This application is based upon and claims the benefit of priority from prior Japanese Patent Application No. 2019-110493, filed Jun. 13, 2019, the entire contents of which are incorporated herein by reference.

FIELD

Embodiments described herein relate generally to an X-ray detection unit for a wheelchair, and an X-ray diagnostic apparatus.

BACKGROUND

The recent social development including aging of population has found increased events of X-ray diagnosis for patients seated in their wheelchairs (may also be called "wheelchair patients" below). In this relation, a chest X-ray examination is often conducted for wheelchair patients, which proceeds in a manner of (A) using a special-purpose wheelchair adapted for X-ray imaging, or (B) having a patient, who remains seated in a normal wheelchair, lean against a Lieder's radiographic stand.

In the manner (A), a special wheelchair for X-ray imaging, furnished with an imaging stand, is employed. This manner involves relocation of the patient from a normal wheelchair to such a special, X-ray imaging-purpose wheelchair, and as such, the patient or the helper must assume an extra burden.

In the manner (B), the patient leaning against the Lieder's radiographic stand is required to take a difficult, inclined stance for the X-ray detector to be operative. Also, since the patient is inclined with respect to the X-ray detector, inadequate X-ray images might result depending on the degree of such inclination.

BRIEF DESCRIPTION OF THE DRAWINGS

FIG. 3 is a side view for explaining certain components of the X-ray detection unit according to the first embodiment.

FIG. 4 is a sectional view based on the arrow 4-4 given in FIG. 2 and the arrow 4-4 given in FIG. 3.

FIG. 5 is a sectional view of a modification of the structure shown in FIG. 4.

FIG. 6 is a sectional view of another modification of the structure shown in FIG. 4.

FIG. 11 is a schematic diagram for explaining certain components of the X-ray detection unit according to the third embodiment.

FIG. 12 is a perspective view of one exemplary design of an X-ray detection unit and a wheelchair according to a modification of the third embodiment.

FIG. 13 is a perspective view of one exemplary design of an X-ray detection unit and a wheelchair according to a fourth embodiment.

FIG. 15 is a schematic diagram showing a configuration of an X-ray diagnostic apparatus including an X-ray detection unit, according to a fifth embodiment.

FIG. 16 is a perspective view of one exemplary design of the X-ray detection unit according to the fifth embodiment.

DETAILED DESCRIPTION

According to one embodiment, an X-ray detection unit for a wheelchair includes a container and an attachment portion coupled with the container. The container is configured to contain a flat X-ray detector. The attachment portion is configured to be detachably mounted to a part of the wheelchair in which a subject is seated, so that a detection plane of the X-ray detector in the container faces the subject.

This can eliminate the necessity of using a special, X-ray imaging-purpose wheelchair, and can also free a patient from the need of taking a difficult stance for X-ray imaging so that the burden on the patient is mitigated.

Now, the embodiments will be described with reference to the drawings.

First Embodiment

Figure 1:
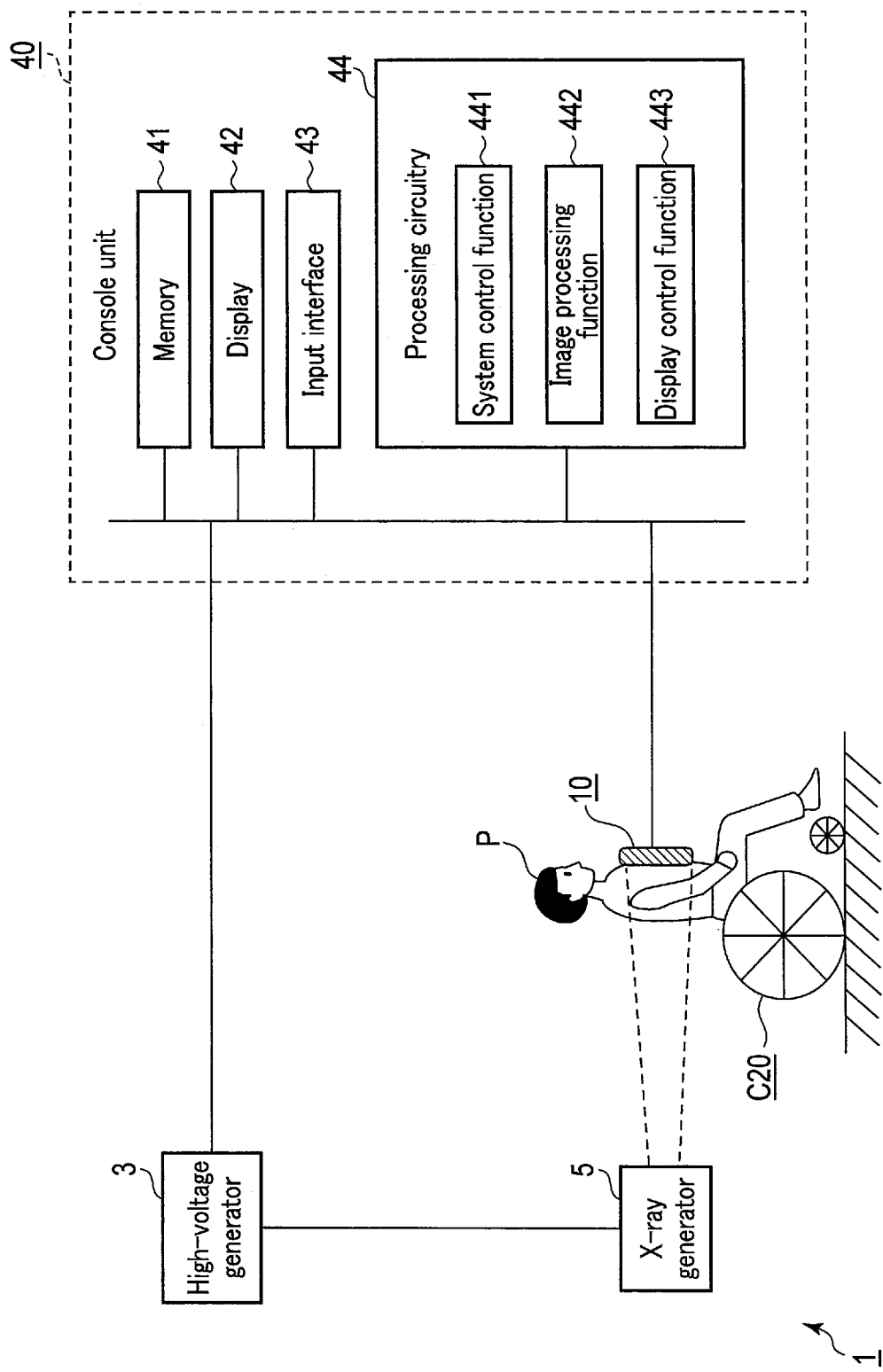
FIG. 1 is a schematic diagram showing a configuration of an X-ray diagnostic apparatus including an X-ray detection unit for a wheelchair, according to a first embodiment.
Figure 2:
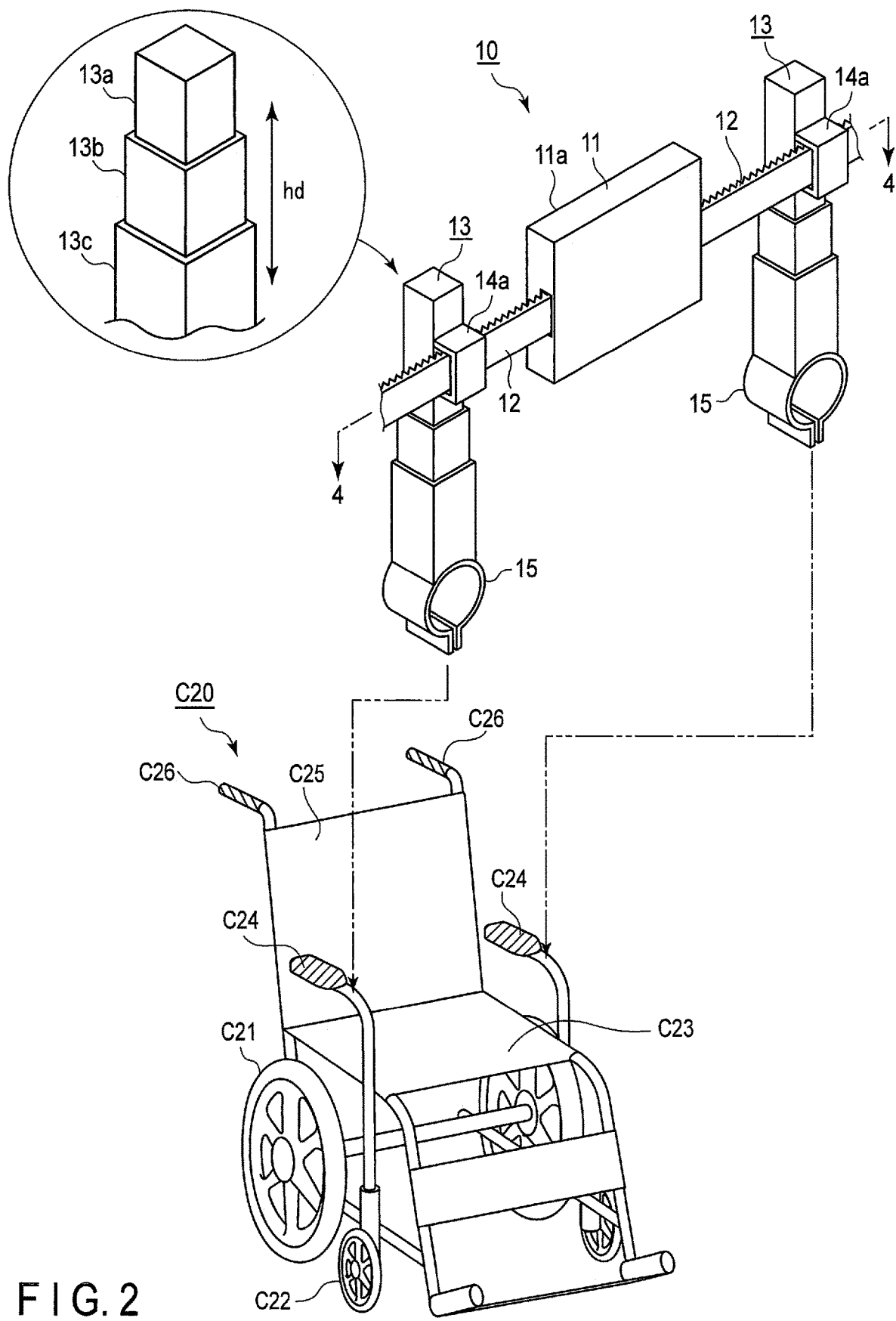
FIG. 2 is a perspective view of one exemplary design of the X-ray detection unit and the wheelchair according to the first embodiment.

FIG. 1 is a schematic diagram showing a configuration of an X-ray diagnostic apparatus including an X-ray detection unit for a wheelchair (may be simply called "X-ray detection unit" below), according to the first embodiment, and FIG. 2 is a perspective view of one exemplary design of the X-ray detection unit and the wheelchair. FIG. 3 is a side view for explaining certain components of the X-ray detection unit, and FIG. 4 is a sectional view based on the arrow 4-4 given in FIG. 2 and the arrow 4-4 given in FIG. 3. The X-ray diagnostic apparatus may also be called a general X-ray imaging apparatus.

The X-ray diagnostic apparatus shown in FIG. 1, which is denoted by reference symbol 1, includes a high-voltage generator 3 and an X-ray generator 5, which are intended to be arranged in an examination room, an X-ray detection unit 10 which is adapted to be attachable to and detachable from a wheelchair, and a console unit 40 which is intended to be arranged in an operation room.

The high-voltage generator 3 includes a various control circuits for controlling a tube current, a tube voltage, an imaging time, etc., as well as components such as a high-voltage transformer, a high-voltage rectifier, and a filament transformer. The high-voltage generator 3 is adapted to generate a tube current to be supplied to an X-ray tube of the X-ray generator 5, and a tube voltage to be applied to the X-ray tube. More specifically, the high-voltage generator 3, under the control of later-described processing circuitry 44 and according to X-ray irradiation conditions, supplies a tube current suitable for X-ray imaging to the X-ray tube and also applies a tube voltage suitable for the X-ray imaging to the X-ray tube. The X-ray irradiation conditions here prescribe values of, for example, the tube current, the tube voltage, irradiation time, a product of the tube current (mA) multiplied by the irradiation time (s) (may also be called "tube current time product (mAs)" below), and so on.

The X-ray generator 5 is supported by a support unit (not illustrated) in such a manner as to be movable in the vertical and horizontal directions and also facing in a desired direction. The X-ray generator 5 is provided with the X-ray tube, and an X-ray diaphragm.

The X-ray tube is adapted to generate X-rays from an X-ray focal point (tube focal point), using a supply of the tube current and an application of the tube voltage from the high-voltage generator 3. The X-rays generated at the tube focal point are radiated toward an irradiation range delimited by the X-ray diaphragm.

The X-ray diaphragm is adapted to delimit the X-ray irradiation range according to an operation by a user, etc. More specifically, the X-ray diaphragm limits the irradiation range to a maximum diameter in accordance with the area of X-ray irradiation on the body surface of a subject P, so that the X-rays generated at the tube focal point will not cause an excessive or unnecessary exposure beyond the imaging target site intended by the user, etc. For example, the X-ray diaphragm limits the irradiation range by moving its diaphragm blades under the control of the processing circuitry 44 and according to a command input from a later-described input interface 43 for limiting the irradiation range.

Note that the X-ray diaphragm may be set with multiple preset filters insertable in front of the X-ray irradiation field, in order to reduce the subject P's dose of exposure and to improve image qualities (such filters may also be called "radiation quality-adjusting filters"). The multiple radiation quality-adjusting filters may have their respective thicknesses differing from one another. Note that the radiation quality-adjusting filters may have the same thickness, while being composed of different materials. The radiation quality-adjusting filters are adapted to alter the radiation quality of the X-rays generated at the tube focal point, according to their thicknesses values. The radiation quality-adjusting filters may be constituted by, for example, aluminum, copper, etc.

The X-ray detection unit 10 is a portable detector device adapted to be set on a subject, e.g., the subject P seated in a wheelchair C20. FIG. 2 presents the X-ray detection unit 10 in a greater magnification ratio than the wheelchair C20. The wheelchair C20 here is a device constituted by drive wheels C21's and casters C22's, by which the subject P resting on a seat C23 can be moved. The wheelchair C20 also includes armrests C24's above the respective sides of the seat C23, for the subject P to place its arms. The wheelchair C20 includes a backrest C25 on the back side of the subject P when seated on the seat C23. There are handles C26's for use by a helper, etc. at the respective end portions of the backrest C25, which are on the side opposite the seat C23 and at a height higher than the seat C23. The backrest C25 is formed of an X-ray transmissive material (e.g., fabric). The wheelchair C20 may be a general wheelchair used in, for example, hospitals, etc. Note that, to facilitate the understanding, the drawings omit detailed structures of such a general wheelchair (e.g., hand rims, tipping lever, lever brake, skirt guards, leg plates, and complex frame portions adopted in practice). The wheelchair C20 may be either a self-maneuvering type provided with hand rims for rotation by hand, or an assisted-movement type without such hand rims.

The X-ray detection unit 10 includes a container 11, a coupling member 12, column members 13's, slide supports 14a's, retentive parts 15's, and an X-ray detector 16, as shown in FIGS. 2 to 4.

The container 11 has an opening (not illustrated) so that the X-ray detector 16, which may be of a flat plate shape, is set in the container 11 through the opening. Among the walls of the container 11, the wall that faces the subject P includes an area 11a corresponding to a detection plane 16a of the X-ray detector 16, and this area 11a is formed of an X-ray transmissive material (e.g., fabric). The walls of the container 11 that do not face the subject P are formed of a rigid material such as metal, plastic, etc. The container 11 in this embodiment is shown to be of a flat box shape as in FIG. 2 or FIG. 4, but the shape of the container 11 is not limited. The container 11 may have any shape discretionarily selected, and examples of such shapes include a shape of a frame with an opening 11b or openings 11b and 11c as shown in FIG. 5 or FIG. 6, a flattened, substantially oval shape without corners, a shape of a bag such as a backpack, and so on. FIG. 5 shows an example where the container 11 has the opening 11b on the side of the detection plane 16a of the X-ray detector 16, and FIG. 6 shows an example where the container 11 has, in addition to this opening 11b, the opening 11c on the side opposite the detection plane 16a of the X-ray detector 16. A space between each rigid-material wall of the container 11 and the X-ray detector 16 set within the container 11 may be filled with a cushion material as appropriate. The container 11 may not have to keep its shape at all times, but may change the shape as, for example, a pouch or a sack.

The coupling member 12 is connected to the container 11, and its longitudinal direction conforms to a width direction wd of the wheelchair C20. The coupling member 12 may be, for example, a plate member having a surface with multiple recesses formed in a saw-tooth pattern as shown in FIG. 4 or formed as patterned dimples or the like. Such recesses may be dents or through-holes. The coupling member 12 is arranged so that this surface faces the column members 13's.

The column members 13's each have the corresponding, respective slide support 14a and retentive part 15 as shown in FIGS. 2 to 4, and the longitudinal direction of each column member 13 conforms to a height direction hd orthogonal to the width direction wd. Here, each column member 13 may be constituted by a first column piece 13a having the slide support 14a at its side face, a second column piece 13b adapted to hold the first column piece 13a in such a manner that the first column piece 13a can be telescopically pushed in and pulled back in the longitudinal direction, and a third column piece 13c adapted to hold the second column piece 13b in such a manner that the second column piece 13b can be telescopically pushed in and pulled back in the longitudinal direction. The third column piece 13c has the retentive part 15 at its end portion opposite the side where the slide support 14*a* is provided. The first column piece 13*a*, the second column piece 13*b*, and the third column piece 13*c* together form a variable-length mechanism that can be contracted and elongated in the longitudinal direction using the sequential telescopic pushing-in movement or pulling-back movement. This variable-length mechanism is one example of a configuration capable of adjusting the position of the container 11 in the height direction hd of the wheelchair C20. Note that the configuration for adjustment in the height direction hd is not limited to the use of such a variable-length mechanism. For example, a substantially cylindrical, hollow component that allows the column member 13 to pass through may be adopted, and the slide support 14*a* may be fixed to the outer periphery of this component so that the slide support 14*a* is movable in the longitudinal direction of the column member 13. This hollow component's substantially cylindrical shape is not required to have a closed profile in cross section (e.g., a substantially circular or quadrilateral profile), but may show a void in part of the profile in cross section (e.g., a substantially "C" profile). Such a structure is another example of the configuration capable of adjusting the position of the container 11 in the height direction hd of the wheelchair C20. Also, as in the case of the present embodiment, the configuration for adjustment in the height direction hd in each of the subsequent embodiments and any modification thereof is not limited to the use of the variable-length mechanism.

The slide supports 14*a*'s are each adapted to support the coupling member 12 so that the coupling member 12 can slide in the width direction wd of the wheelchair C20 as shown in FIGS. 2 to 4. The slide supports 14*a*'s face their respective positioning mechanisms 14*b*'s through the coupling member 12.

The positioning mechanisms 14*b*'s are each provided with a projecting part and adapted to press this projecting part by an elastic force from a spring, etc. onto the surface of the coupling member 12 where the multiple recesses are formed, so that the coupling member 12 is latched and stops the sliding movement. Each positioning mechanism 14*b* may be, for example, a plunger such as a ball plunger or a pin plunger, or a plate spring member having one end projected from the column member 13, but this is not a limitation. Also, while the drawings show each positioning mechanism 14*b* as a component arranged inside the corresponding column member 13, the positioning mechanisms 14*b*'s may be provided on the side faces of the respective column members 13's. The description of this embodiment assumes each positioning mechanism 14*b* to be a ball plunger embedded in the corresponding column member 13.

The retentive parts 15's are each adapted to detachably retain the corresponding, respective handle C26 or armrest C24 of the wheelchair C20. For example, each retentive part 15 may include, for retention, substantially vaulted semi-cylindrical or cylindrical portions to clamp the handle C26 or the armrest C24, which may be of a substantially round pipe shape. The retentive part 15 may then release the handle C26 or the armrest C24 by unclamping. Instead of such a clamping structure, the retentive part 15 may include a substantially cylindrical structure for retaining the handle C26 or the armrest C24 in such a manner as to sheathe the handle C26 or the armrest C24 from one end.

Note that the coupling member 12, the column members 13's, the slide supports 14*a*'s, and the retentive parts 15's together constitute one example of an attachment portion. The attachment portion is coupled with the container 11 and is attachable to a part of the wheelchair C20 in which the subject P is seated, so that the detection plane 16*a* of the X-ray detector 16 set in the container 11 faces the subject P. For example, the attachment portion may be attached to the handles C26's or the armrests C24's of the wheelchair C20. For this first embodiment and the subsequent second embodiment, the description will assume the instances of attaching the attachment portion to the armrests C24's. For the third embodiment and the fourth embodiment, the description will assume the instances of attaching the attachment portion to either only the handles C26's, or both the handles C26's and the armrests C24's. Additionally, the coupling member 12, the column members 13's, and the slide supports 14*a*'s together constitute one example of a configuration capable of adjusting the positions of the retentive parts 15's in the width direction wd of the wheelchair C20.

The X-ray detector 16 may be a portable, flat plate-type X-ray detector (also called a flat panel detector (FPD)) that can be accommodated in the container 11 and set for the subject P seated in the wheelchair C20. The X-ray detector 16 is adapted to detect the X-rays which have been generated by the X-ray tube at the X-ray generator 5, shaped by the X-ray diaphragm for radiation toward the subject P, and transmitted through the subject P, and to output X-ray image data. The X-ray detector 16 includes a planar detector constituted by multiple semiconductor detecting elements, as well as an analog-to-digital converter (hereinafter, "A/D converter"), image generating circuitry, and an image memory. The semiconductor detecting elements may be either a direct conversion type or an indirect conversion type. The direct conversion type refers to converting incident X-rays directly into electric signals. The indirect conversion type refers to converting incident X-rays into light using a fluorescent material and then converting the light into electric signals. Regardless of such difference in type, the multiple semiconductor detecting elements produce electric signals according to the incoming X-rays and output the electric signals to the A/D converter. The A/D converter is adapted to convert the input electric signals into digital data and output the digital data to the image generating circuitry. The image generating circuitry is adapted to generate X-ray image data based on the digital data and output the X-ray image data to the image memory. The X-ray image data in the image memory is output to the console unit 40.

The console unit 40 includes a memory 41 and a display 42, as well as the aforementioned input interface 43 and processing circuitry 44.

The memory 41 includes a memory main component for storing electric information, such as a read only memory (ROM), a random access memory (RAM), a hard disk drive (HDD), an image memory, etc. The memory 41 also includes peripheral circuitry pertaining to the memory main component, such as a memory controller, a memory interface, etc. The memory 41 stores, for example, X-ray irradiation conditions as discussed above, X-ray images before image processing which are received from the X-ray detector 16, X-ray images after image processing which are received from the processing circuitry 44, various tables, data under processing, data after processing, programs for the processing circuitry 44, and so on. The memory 41 is one example of a storage.

The display 42 includes a display main component for displaying various information items including the X-ray irradiation conditions, the X-ray images, etc., internal circuitry for supplying display signals to the display main component, and peripheral circuitry including connectors, cables, or the like for connection between the display main component and the internal circuitry. The internal circuitry is adapted to generate display data by superimposing supplemental information, such as information on the subject, the X-ray irradiation conditions, etc., on the X-ray image given from the processing circuitry 44, and to subject this display data to D/A conversion and TV format conversion for display through the display main component. For example, the display 42 outputs the X-ray images provided from the processing circuitry 44, graphical user interfaces (GUIs) for accepting various operations from an operator, and so on. Examples of the display 42 include a liquid crystal display and a cathode ray tube (CRT) display. Also, the display 42 may be a desktop type, or implemented as a tablet terminal or the like capable of wireless communications with a substantial part of the console unit 40. The display 42 is one example of a display.

The input interface 43 enables input of the subject information, setting of the X-ray irradiation conditions, etc., input of various command signals, and so on. The subject information includes, for example, a subject ID as well as the subject's name, date of birth, age, weight, gender, site for examination, etc. The subject information may further include the subject's height. Also, the various command signals may include an ON signal and an OFF signal for X-ray imaging. For example, the input interface 43 follows the operator's operation to input such an ON signal or OFF signal for X-ray imaging. The input interface 43 is realized by components for providing, for example, instructions for movement with respect to the X-ray generator 5, setting of a region of interest (ROI), etc., and such components include a trackball, switch buttons, a mouse, a keyboard, a touch pad which allows an input operation through contacting its operation screen, and a touch panel display which integrates a display screen and a touch pad. The input interface 43 is connected to the processing circuitry 44, and adapted to convert input operations received from the operator into electric signals and to output the electric signals to the processing circuitry 44. The input interface 43 may instead be implemented as a tablet terminal or the like capable of wireless communications with a substantial part of the console unit 40. In the present disclosure, the input interface 43 is not limited to physical operating components such as a mouse and a keyboard. That is, the examples of the input interface 43 also include processing circuitry for electric signals, which is adapted to receive an electric signal corresponding to an input operation from an external input device separate from the apparatus unit, and to output this electric signal to the processing circuitry 44. The input interface 43 is one example of an inputter.

The processing circuitry 44 is adapted to read the various information items and the programs from the memory 41 according to an instruction input by the operator through the input interface 43, and to control the X-ray diagnostic apparatus 1 based on these. For example, the processing circuitry 44 is a processor to realize various functions including a system control function 441 for X-ray imaging, an image processing function 442, a display control function 443, etc., according to the programs read from the memory 41. Note that the display control function 443 and the display 42 may be mounted on other computer (not illustrated) instead of the console unit 40. In such instances, for example, the console unit 40 may operate as a server device, and said other computer may operate as a client device that displays the X-ray images generated by the server device.

The system control function 441, for example, handles information such as command signals or various initial setting and conditions input via the input interface 43 from an operator, in such a manner that it temporarily holds the information and then sends the information to the respective, corresponding functions. The command signals here include an ON signal and an OFF signal for X-ray imaging, as mentioned.

In an exemplary case, the system control function 441 controls the X-ray generator 5 using information input via the input interface 43 in relation to driving of the X-ray generator 5. In this case, the system control function 441 controls, for example, the movement of the X-ray detector 5 and the actions of the X-ray diaphragm, etc.

In another exemplary case, the system control function 441 controls the high-voltage generator 3 for the X-ray irradiation conditions including values of the tube voltage, the tube current, the irradiation time, etc., upon reading the information in the memory 41. The X-ray irradiation conditions may include a product (mAS) of the tube current and the irradiation time. The control for the X-ray irradiation conditions includes controlling the X-ray generator 5 to start X-ray imaging and also to stop the X-ray imaging.

The image processing function 442 performs image processing such as corrections on the X-ray image data (projection data) received from the X-ray detection unit 10, and sends the resultant X-ray image (X-ray image data having been subjected to the image processing) to the display control function 443. Examples of the image processing also include offset corrections and gain corrections for the X-ray detector 16, noise reduction, dynamic range compression, edge enhancement, gradation adjustment, etc.

The display control function 443 causes the display 42 to display various information items and images according to the processing of the processing circuitry 44. For example, the display control function 443 causes the display 42 to display the X-ray images received from the image processing function 442. Furthermore, examples of the control, etc. performed by the display control function 443 include reading signals from the system control function 441, acquiring desired image data and information items, etc. from the memory 41, and displaying them through the display 42.

Figure 7:
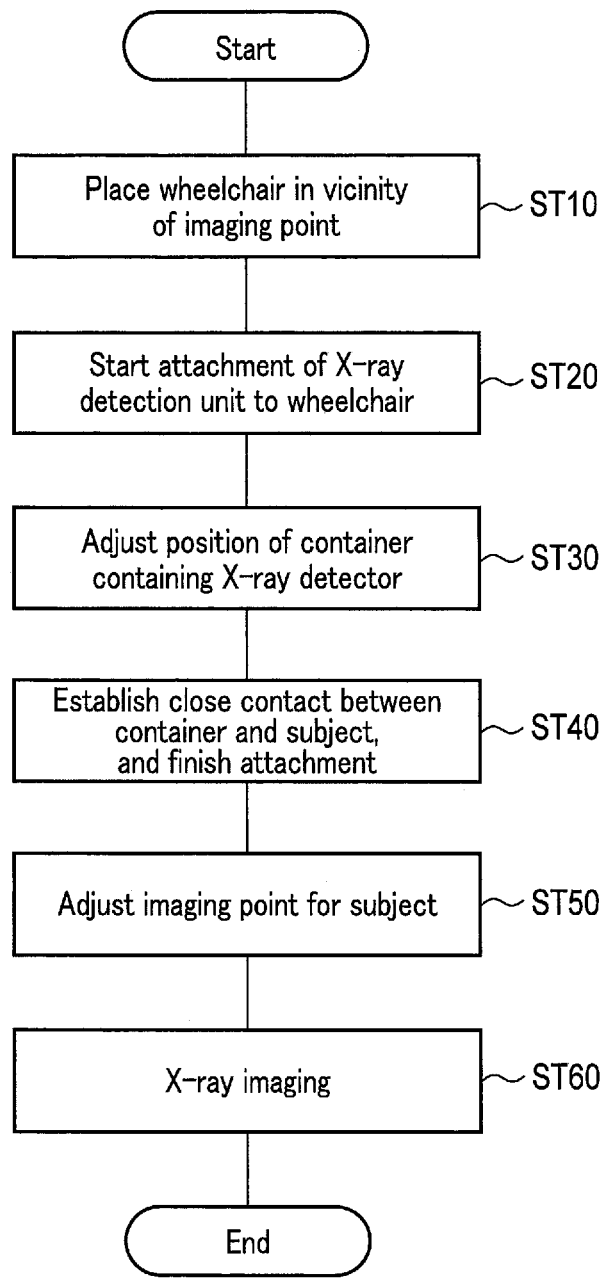
FIG. 7 is a flowchart for explaining one exemplary operation of the X-ray diagnostic apparatus according to the first embodiment.

Next, operations associated with the X-ray diagnostic apparatus 1 configured as above will be described with reference to the flowchart of FIG. 7. The description will basically concentrate on operations related to the X-ray detection unit 10 to be mounted, including the attachment of the X-ray detection unit 10 and the subsequent start of X-ray imaging.

It will be supposed that, firstly, preparation for imaging is done by acquiring the subject information including, for example, a patient ID and a site for examination, and setting the X-ray irradiation conditions, etc. Upon becoming prepared for imaging, operations of step ST10 and onward are performed.

In step ST10, the wheelchair C20 in which the patient, i.e., the subject P, is seated is arranged in the vicinity of the imaging point. As a guide of the imaging point, for example, the floor face, etc. may show a mark indicative of the use for wheelchairs.

In step ST20 after step ST10, the attachment of the X-ray detection unit 10 to the wheelchair C20 is initiated.

In step ST30 after step ST20, the position of the container 11 set with the X-ray detector 16 is adjusted. More concretely, the retentive parts 15's are attached to the respective armrests C24's in an orientation where the detection plane 16a of the X-ray detector 16 set in the container 11 faces the subject P. At this time, the position of the container 11 in the height direction hd may be adjusted by having the column members 13's elongated or contracted as needed. The container 11 is then caused to slide in the width direction wd of the wheelchair C20 for a desired position.

In step ST40 after step ST30, a close contact between the container 11 and the subject P is established, thereby completing the attachment. More concretely, and for example, the container 11 can be placed in close contact with the subject P by directing the subject P to hold the container 11 in its arms.

In step ST50 after step ST40, the imaging point for the subject P is adjusted while the close contact between the container 11 and the subject P is maintained. More concretely, the imaging point for the subject P can be adjusted by, for example, the operator, etc. moving the wheelchair C20 together with the seated subject P.

In step ST60 after step ST50, the X-ray generator 5 irradiates the subject P with X-rays and then the X-ray detector 16 detects the X-rays transmitted through the subject P, so that the subject P undergoes X-ray imaging. The X-ray image data output from the X-ray detector 16 is subjected to image processing by the processing circuitry 44. The X-ray image obtained after the image processing is displayed by the display 42 under the control of the processing circuitry 44. The X-ray imaging is complete upon, for example, the operator, etc., confirming the displayed X-ray image.

According to the first embodiment as described above, the container 11 contains the flat X-ray detector 16, and the attachment portion is coupled with the container 11 and detachably mounted to the armrests C24's of the wheelchair C20 in which the subject P is seated, so that the detection plane 16a of the X-ray detector 16 set in the container 11 faces the subject P. Thus, the first embodiment can eliminate the necessity of using a special, X-ray imaging-purpose wheelchair, and can also free a patient from the need of taking a difficult stance for X-ray imaging so that the burden on the patient is mitigated.

Also according to the first embodiment, the attachment portion is constituted by the multiple retentive parts 15's for detachably retaining the respective armrests C24's, and has a configuration that enables the positions of the retentive parts 15's to be adjusted in the width direction wd of the wheelchair C20. Thus, in addition to the above effects, the first embodiment provides a further effect that the X-ray detection unit 10 has a width for mounting that is adjustable according to the width of the wheelchair C20.

The first embodiment forms such a configuration for adjustment in the width direction wd by using: the coupling member 12 connected to the container 11 and having a longitudinal direction conforming to the width direction wd; the slide supports 14a's supporting the coupling member 12 to be slidable in the width direction wd; and the column members 13's each having the corresponding, respective slide support 14a and retentive part 15 and both having a longitudinal direction conforming to the height direction hd orthogonal to the width direction wd. Thus, in addition to the adjustable mounting width of the X-ray detection unit 10, the first embodiment allows the position of the container 11 to be adjusted by the sliding movement in the width direction wd.

According to the first embodiment, moreover, the attachment portion also has a configuration that enables the position of the container 11 to be adjusted in the height direction hd of the wheelchair C20. Thus, in addition to the above effects, the first embodiment provides a further effect that the mounting to the wheelchair C20 can be done with the position of the container 11 suitably adjusted according to the sitting height, etc. of the subject P.

The first embodiment forms such a configuration for adjustment in the height direction hd by using the variable-length mechanism. Thus, in addition to the above effects, the first embodiment even permits the X-ray detection unit 10 to be compacted after examination and stored without requiring a large space.

Second Embodiment

Figure 8:
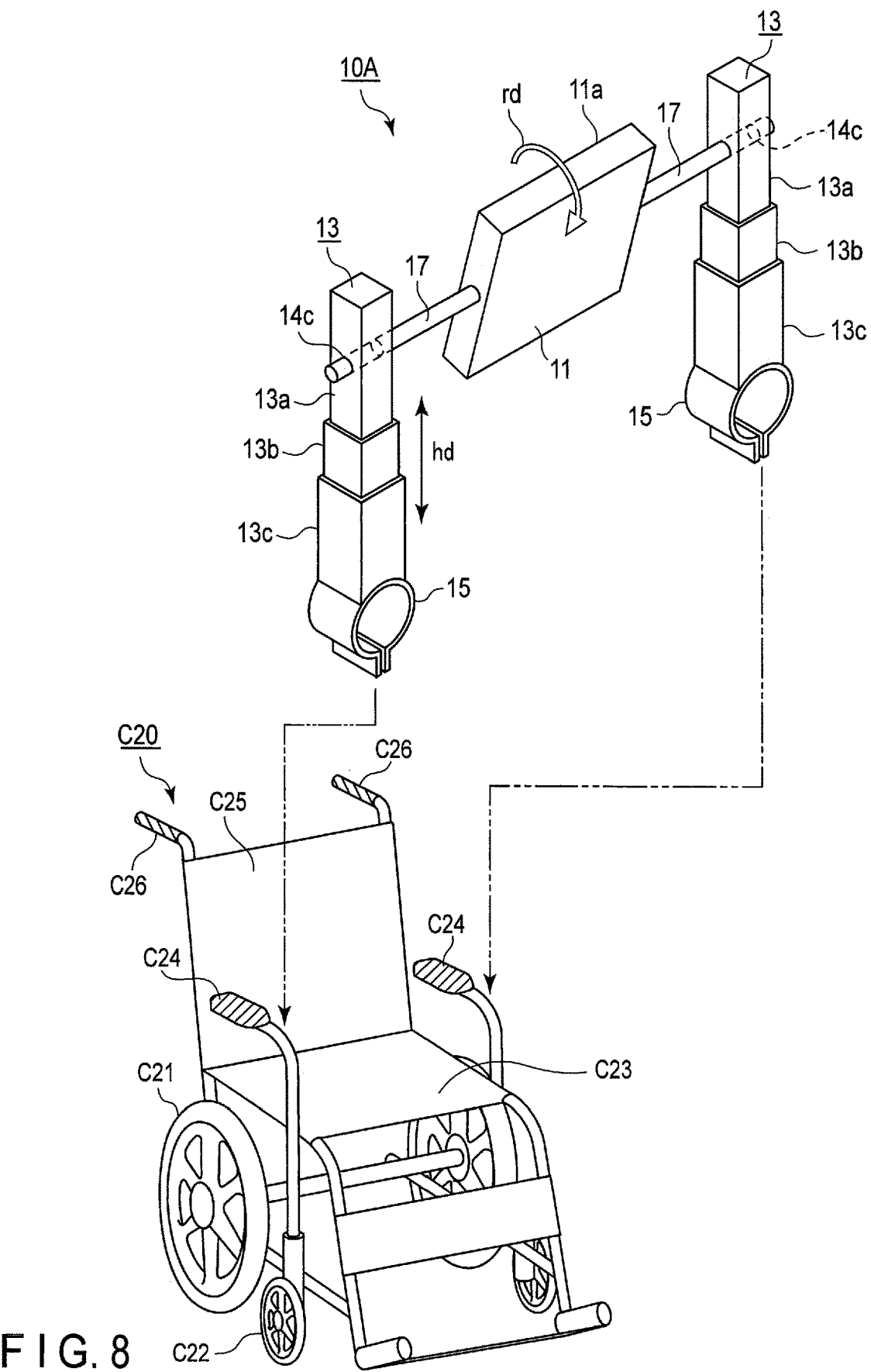
FIG. 8 is a perspective view of one exemplary design of an X-ray detection unit and a wheelchair according to a second embodiment.
Figure 9:
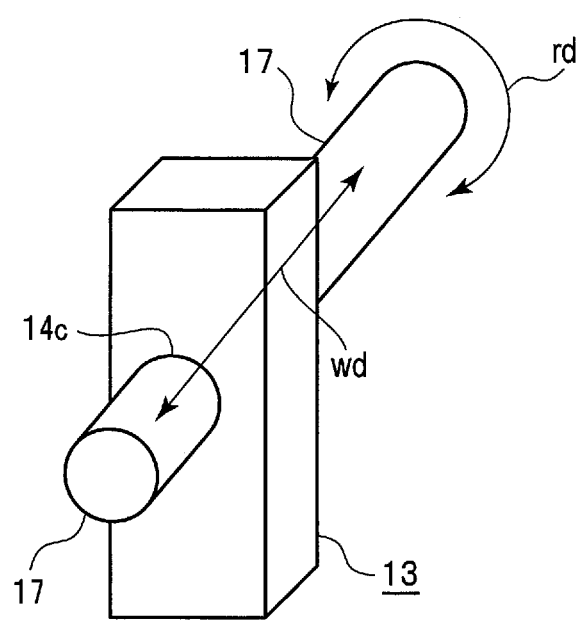
FIG. 9 is a schematic diagram for explaining certain components of the X-ray detection unit according to the second embodiment.

The second embodiment will be described next, with reference to FIGS. 8 and 9. The description will use same reference symbols for the components or operational features of the same, or substantially the same, contents that appear in the already discussed drawings. The description will in principle omit the details of such components, etc., and concentrate on the portions differing from the foregoing embodiment. The subsequent embodiments will each be described in the same manner, and redundant explanations will be omitted.

The second embodiment may be understood as a modification of the first embodiment, where an X-ray detection unit 10A including a rod member 17 as a coupling member is adopted in place of the X-ray detection unit 10 with the plate-like coupling member 12 according to the first embodiment. The rod member 17 is connected to the container 11 and held by the column members 13's via through-holes 14c's so that the rod member 17 can rotate about its longitudinal axis. More specifically, as shown in FIG. 9, the rod member 17 is held via the through-holes 14c's of the respective column members 13's so that it is rotatable in a circumferential direction rd with respect to the longitudinal axis and also slidable in the width direction wd of the wheelchair C20. The circumferential direction rd with respect to the longitudinal axis here may also be called a direction of forward inclination for the subject P or a direction of forward rotation, or a direction of backward rotation, etc. as well. The slide support 14a and the positioning mechanism 14b as in the foregoing embodiment may be omitted. The rod member 17, the column members 13's, the through-holes 14c's, and the retentive parts 15's together constitute another example of the attachment portion.

The remaining aspects are the same as the first embodiment.

With this configuration, steps ST10 to ST60 can be performed for the subject P seated in the wheelchair C20 in the similar manner as discussed above, using the X-ray detection unit 10A that permits the container 11 set with the X-ray detector 16 to rotate in the forward-inclination direction for the subject P. Note that when, for example, the subject P is inclined forward, step ST50 of adjusting the imaging point for the subject P should include adjusting the orientation of the X-ray generator 5 so that the X-ray tube squarely face toward the X-ray detector 16 placed in close contact with the inclined subject P. The operation flow then proceeds with step ST60 of performing X-ray imaging in the similar manner as discussed.

According to the second embodiment as described above, the same effects and advantages as in the first embodiment can be obtained using the configuration where the member for coupling is changed from the plate-like coupling member 12 to the rod member 17. Moreover, the second embodiment realizes the rotatable structure by the rod member 17, and can therefore enable X-ray imaging to be performed for even the subject P who is in an inclined state.

Third Embodiment

Figure 10:
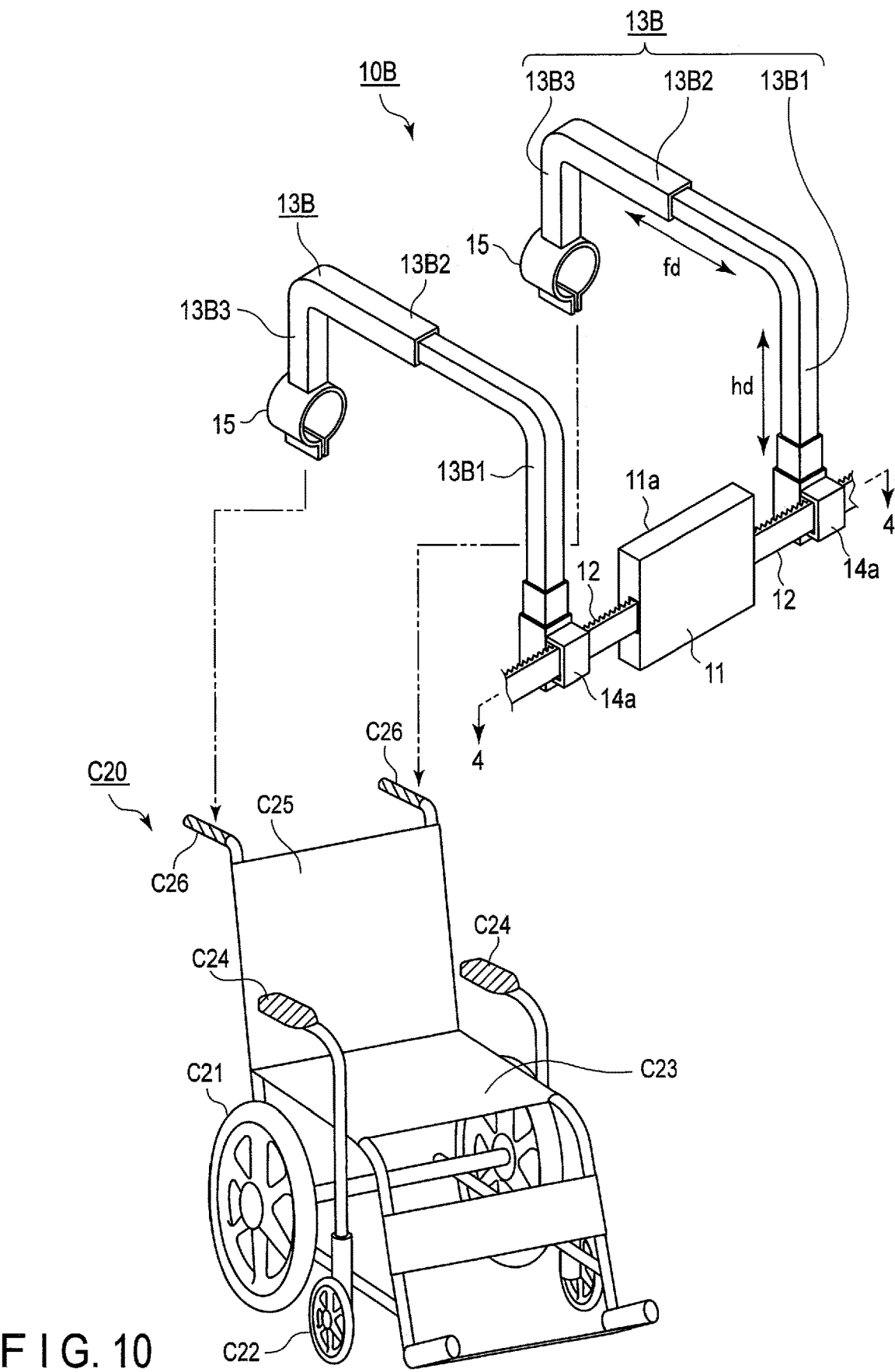
FIG. 10 is a perspective view of one exemplary design of an X-ray detection unit and a wheelchair according to a third embodiment.

An X-ray diagnostic apparatus including an X-ray detection unit according to the third embodiment will be described with reference to FIGS. 10 and 11.

The third embodiment may be understood as a modification of the first embodiment, where an X-ray detection unit 10B including an attachment portion adapted to be detachably mounted to the handles C26's is adopted in place of the X-ray detection unit 10 including the attachment portion adapted to be detachably mounted to the armrests C24's according to the first embodiment. Accordingly, the third embodiment uses a configuration where the column members 13's have been replaced with connection members 13B's each having a substantially inverted-"L" shape and connecting the corresponding retentive part 15 for retaining the handle C26 with the corresponding slide support 14a for supporting the coupling member 12.

Each connection member 13B is constituted by a first column member 13B1 corresponding to a longer vertical axis of the substantially inverted-"L" shape, a second column member 13B2 corresponding to a horizontal axis of the substantially inverted-"L" shape, and a third column member 13B3 corresponding to a shorter vertical axis of the substantially inverted-"L" shape. The connection members 13B's here are each assumed to be including the first column member 13B1, the second column member 13B2, and the third column member 13B3 constructed as a combination or the like of multiple bent pipe members. However, this is not a limitation. For example, the connection member 13B may include the first column member 13B1, the second column member 13B2, and the third column member 13B3 which are formed integrally from a single pipe member bent as appropriate.

The first column member 13B1 is provided with the slide support 14a and the positioning mechanism 14b (not illustrated) at its lower side face as in the foregoing embodiment, and the upper end of the first column member 13B1 is connected with one end of the second column member 13B2. The first column member 13B1 may include multiple column pieces similar to the first column piece 13a, the second column piece 13b, and the third column piece 13c described for the foregoing embodiment, so that these multiple column pieces together form a variable-length mechanism that can be contracted and elongated in the longitudinal direction using sequential telescopic pushing-in movement or pulling-back movement. The variable-length mechanism is one example of a configuration capable of adjusting the position of the container 11 in the height direction hd of the wheelchair C20. This variable-length mechanism for the height direction hd is not an essential feature and may be omitted.

The second column member 13B2 has its variable-length mechanism that can be contracted and elongated in the longitudinal direction by utilizing a configuration where a rear-side column piece 13d holds a front-side column piece 13e in such a manner that the front-side column piece 13e can be telescopically pushed in and pulled back. This variable-length mechanism is one example of a configuration capable of adjusting the position of the container 11 in a front-and-back direction fd of the wheelchair C20. The configuration for adjustment in the front-and-back direction fd is not an essential feature and may be omitted. When indeed omitted, the adjustment may be done by, for example, shifting the retentive parts 15's retaining the handles C26's in the front-and-back direction fd. These two column pieces 13d and 13e can be locked and stabilized by means of a screw 13f provided on the outer column piece, i.e., the column piece 13d, such that the tip portion of the screw 13f presses the inner column piece 13e. However, the technique or configuration to stabilize the column pieces 13d and 13e is not limited to this. For example, the outer column piece 13d may include one first hole and the inner column piece 13e may include multiple second holes arranged in the longitudinal direction, so that the two column pieces 13d and 13e can be pinned together and stabilized via a through-hole formed by the first hole and one second hole overlapping each other at a suitable position. That is, the two column pieces 13d and 13e may be fixed by other means than the screw 13f. Besides, the two column pieces 13d and 13e may not have to be firmly fixed, but may instead adopt respective materials that would prevent each other from slipping. The front-side column piece 13e has its distal end connected to the upper end of the first column member 13B1, and its proximal end held by the rear-side column piece 13d in such a manner that the front-side column piece 13e can be pushed in and pulled back. The rear-side column piece 13d has a distal end adapted to hold the proximal end of the front-side column piece 13e in such a manner that the front-side column piece 13e can be pushed in and pulled back. The rear-side column piece 13d has its proximal end connected to the upper end of the third column member 13B3.

The third column member 13B3 is thus connected at its upper end to the second column member 13B2, and its proximal end has the retentive part 15. Here, the retentive part 15 forms an angle according to the longitudinal axis of the corresponding handle C26. More specifically, and for example, the retentive part 15 is held by the third column member 13B3 at an angle so that the longitudinal axis of the handle C26 and the center axis of the cylindrical portion of the retentive part 15 coincide with each other. According to the exemplary design shown in FIG. 10, the angle formed between the (substantially horizontal) center axis of the cylindrical portion of the retentive part 15 and the (substantially vertical) longitudinal axis of the third column member 13B3 is approximately 90°. This angle varies depending on the longitudinal axis of the handle C26 and the longitudinal axis of the third column member 13B3, so it is not limited to approximately 90°. For example, when the longitudinal axis of the handle C26 is inclined at $\theta°$ from the substantially horizontal axis, and the longitudinal axis of the third column member 13B3 is a substantially vertical axis, this angle of the retentive part 15 is approximately $90°\pm\theta°$. Also, for example, even when the longitudinal axis of the handle C26 is inclined at $\theta°$ from the substantially horizontal axis, the angle of the retentive part 15 is approximately 90° as long as the longitudinal axis of the third column member 13B3 is inclined at $\theta°$ from the substantially vertical axis. In the latter case, an angle formed between the longitudinal axis of the third column member 13B3 and the (substantially horizontal) longitudinal axis of the second column member 13B2 may be $90°-\theta°$. In any case, the third column member 13B3 is attached to the corresponding handle C26 via the retentive part 15. This applies to each of the subsequent embodiments. The coupling member 12, the connection members 13B's, slide supports 14a's, and the retentive parts 15's together constitute yet another example of the attachment portion.

The remaining aspects are the same as the first embodiment.

With this configuration, steps ST10 to ST60 can be performed for the subject P seated in the wheelchair C20 in the similar manner as discussed for the first embodiment, using the X-ray detection unit 10B that permits the container 11 set with the X-ray detector 16 to be detachably mounted on each of the handles C26's through the attachment portion. Note that, in step ST30, the retentive parts 15's are attached to the handles C26's, respectively. At this time, the position of the container 11 in the height direction hd and/or the front-and-back direction fd may be adjusted by having the connection members 13B's elongated or contracted as needed. The container 11 is also caused to slide in the width direction wd of the wheelchair C20 for a desired position. The operation flow then proceeds with step ST40 and onward in the similar manner as discussed.

According to the third embodiment as described above, the container 11 contains the flat X-ray detector 16, and the attachment portion is coupled with the container 11 and detachably mounted to the handles C26's of the wheelchair C20 in which the subject P is seated, so that the detection plane 16a of the X-ray detector 16 set in the container 11 faces the subject P. Thus, the third embodiment can eliminate the necessity of using a special, X-ray imaging-purpose wheelchair, and can also free a patient from the need of taking a difficult stance for X-ray imaging so that the burden on the patient is mitigated.

Also according to the third embodiment, the attachment portion is constituted by the multiple retentive parts 15's for detachably retaining the respective handles C26's, and has a configuration that enables the positions of the retentive parts 15's to be adjusted in the width direction wd of the wheelchair C20. Thus, in addition to the above effects, the third embodiment provides a further effect that the X-ray detection unit 10B has a width for mounting that is adjustable according to the width of the wheelchair C20.

The third embodiment forms such a configuration for adjustment in the width direction wd by using: the coupling member 12 connected to the container 11 and having a longitudinal direction conforming to the width direction wd; the slide supports 14a's supporting the coupling member 12 to be slidable in the width direction wd; and the first connection members 13B1's each having the corresponding, respective slide support 14a and retentive part 15 and both having a longitudinal direction conforming to the height direction hd orthogonal to the width direction wd. Thus, in addition to the adjustable mounting width of the X-ray detection unit 10B, the third embodiment allows the position of the container 11 to be adjusted by the sliding movement in the width direction wd.

According to the third embodiment, moreover, the attachment portion also has a configuration that enables the position of the container 11 to be adjusted in the height direction hd of the wheelchair C20. Thus, in addition to the above effects, the third embodiment provides a further effect that the mounting to the wheelchair C20 can be done with the position of the container 11 suitably adjusted according to the sitting height, etc. of the subject P.

The third embodiment forms such a configuration for adjustment in the height direction hd by using the variable-length mechanism. Thus, in addition to the above effects, the third embodiment even permits the X-ray detection unit 10B to be compacted after examination and stored without requiring a large space.

According to the third embodiment, still more, the attachment portion further has a configuration that enables the position of the container 11 to be adjusted in the front-and-back direction fd of the wheelchair C20. Thus, in addition to the above effects, the third embodiment realizes a further additional effect that the mounting to the wheelchair C20 can be done with the position of the container 11 suitably adjusted according to the chest circumference, waist circumference, etc. of the subject P.

The third embodiment forms this configuration for adjustment in the front-and-back direction fd by using the variable-length mechanism. Thus, in addition to the above effects, the third embodiment permits the X-ray detection unit 10B to be compacted to a greater degree after examination, and stored without requiring a large space.

The third embodiment as such may be modified so that the X-ray detection unit 10B is replaced with an X-ray detection unit 10Bx having a configuration as shown in FIG. 12 that includes two additional retentive parts 15's for detachably retaining the respective armrests C24's. According to this modification, the attachment portion is adapted to be attached via four points, i.e., the handles C26's and the armrests C24's. Therefore, in addition to the effects and advantages as discussed for the first and the third embodiments, the modification realizes a further advantage of placing the patient P in a more secure and stable posture using the configuration of very firmly mounting the X-ray detection unit 10Bx on the wheelchair C20.

Fourth Embodiment

An X-ray diagnostic apparatus including an X-ray detection unit according to the fourth embodiment will be described with reference to FIG. 13.

The fourth embodiment may be understood as a combination of the second embodiment and the third embodiment, and will be described as a modification of the third embodiment (while describing it as a modification of the second embodiment is also possible). The fourth embodiment, as being a modification of the third embodiment, adopts an X-ray detection unit 10C including a rod member 17 as a coupling member, in place of the X-ray detection unit 10B including the plate-like coupling member 12. The rod member 17 is connected to the container 11 and held by the connection members 13B's via through-holes 14c's so that the rod member 17 can rotate about its longitudinal axis. More specifically, as shown in previously-discussed FIG. 9, the rod member 17 is held via the through-holes 14c's of the respective connection members 13B's so that it is rotatable in a circumferential direction rd with respect to the longitudinal axis and also slidable in the width direction wd of the wheelchair C20. The circumferential direction rd with respect to the longitudinal axis here may also be called a direction of forward inclination for the subject P or a direction of forward rotation, or a direction of backward rotation, etc. as well. The slide support 14a and the positioning mechanism 14b as in the first embodiment may be omitted. The rod member 17, the connection members 13B's, the through-holes 14c's, and the retentive parts 15's together constitute yet another example of the attachment portion.

The remaining aspects are the same as the third embodiment.

With this configuration, steps ST10 to ST60 can be performed for the subject P seated in the wheelchair C20 in the similar manner as discussed for the second embodiment, using the X-ray detection unit 10C that permits the container 11 set with the X-ray detector 16 to rotate in the forward-inclination direction for the subject P. Note that, in step ST30, the retentive parts 15's are attached to the handles C26's, respectively. At this time, the position of the container 11 in the height direction hd and/or the front-and-back direction fd may be adjusted by having the connection members 13B's elongated or contracted as needed. The container 11 is also caused to slide in the width direction wd of the wheelchair C20 for a desired position. The operation flow then proceeds with step ST40 and onward in the similar manner as discussed.

According to the fourth embodiment as described above, the same effects and advantages as in the third embodiment can be obtained using the configuration where the member for coupling is changed from the plate-like coupling member 12 to the rod member 17. Moreover, the fourth embodiment realizes the rotatable structure by the rod member 17, and can therefore enable X-ray imaging to be performed for not only the subject P with its back kept straight but also the subject P in an inclined state. In other words, the fourth embodiment can provide the same effects and advantages as in the second and the third embodiments.

Figure 14:
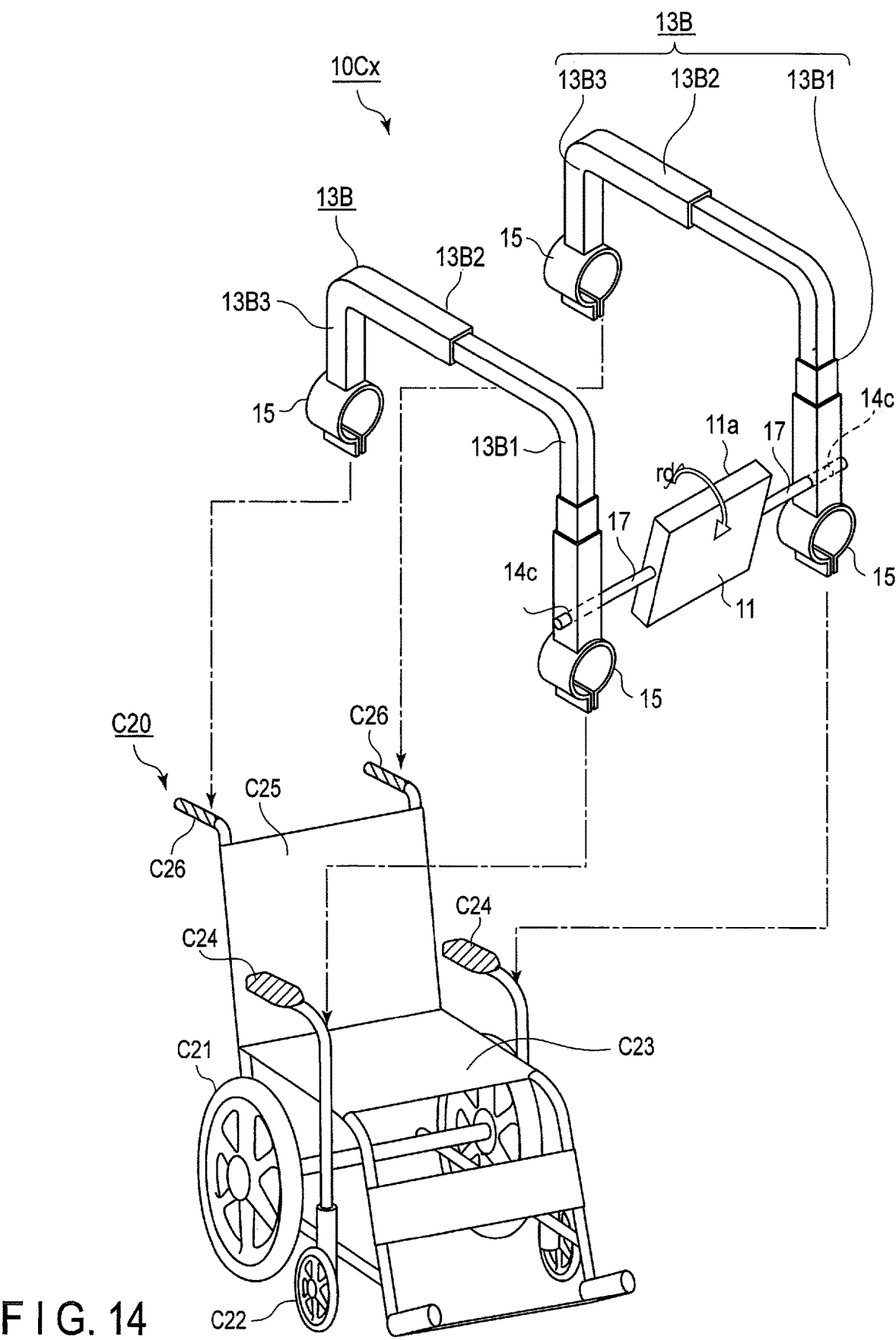
FIG. 14 is a perspective view of one exemplary design of an X-ray detection unit and a wheelchair according to a modification of the fourth embodiment.

The fourth embodiment as such may be modified so that the X-ray detection unit 10C is replaced with an X-ray detection unit 10Cx having a configuration as shown in FIG. 14 that includes two additional retentive parts 15's for detachably retaining the respective armrests C24's. According to this modification, the attachment portion is adapted to be attached via four points, i.e., the handles C26's and the armrests C24's. Therefore, in addition to the effects and advantages as discussed for the second and the third embodiments, the modification realizes a further advantage of placing the patient P in a more secure and stable posture using the configuration of very firmly mounting the X-ray detection unit 10Cx on the wheelchair C20.

Fifth Embodiment

An X-ray diagnostic apparatus including an X-ray detection unit according to the fifth embodiment will be described with reference to FIGS. 15 to 18.

Figure 17:
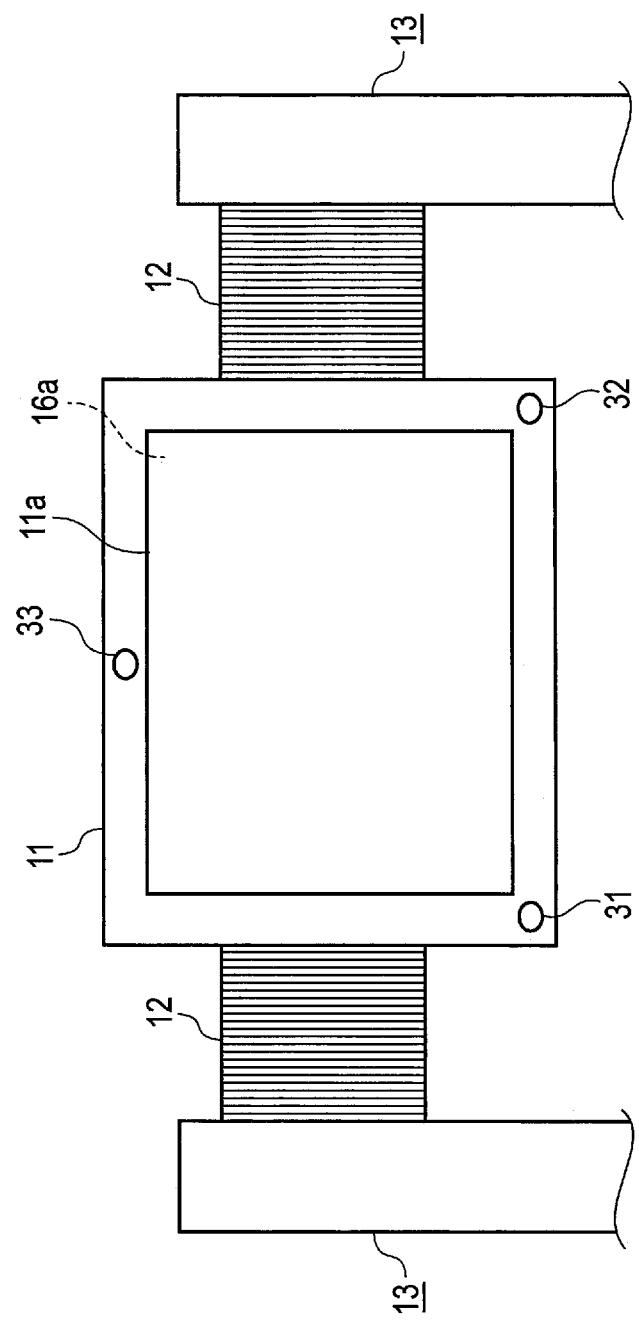
FIG. 17 is a front view of certain components of the X-ray detection unit according to the fifth embodiment.

The fifth embodiment may be understood as a modification of the first embodiment, and it additionally employs, in order to check the position of the X-ray detection unit 10, three position sensors 31 to 33 each provided at the peripheral portion of the area 11a of the container 11 that faces the detection plane 16a of the X-ray detector 16 as shown in FIGS. 15 to 18. For example, these position sensors 31 to 33 are arranged at respective corners of a triangle having a base substantially conforming to the lower side of the container 11 as shown in FIG. 17. Note that the number of position sensors to be employed are not limited to three, and four or more position sensors may be discretionarily used. The console unit 40 according to this embodiment additionally includes acquisition circuitry 45, and the processing circuitry 44 additionally has a determination function 444.

The position sensors 31 to 33 are adapted to acquire position signals for the X-ray detector 16. More specifically, the position sensors 31 to 33 each acquire position signals which are based on a predetermined reference position. Each position signal is a detection signal corresponding to the position of the respective one of the position sensors 31 to 33 with respect to the predetermined reference position. The predetermined reference position may be, for example, the position of a signal transmitter (not illustrated). Such a transmitter is adapted to transmit reference signals for detection by the position sensors 31 to 33. Examples of the transmitter which may be used here include a magnetic transmitter for generating magnetism, an infrared transmitter for generating infrared rays, or the like. The position sensors 31 to 33 output the acquired position signals to the acquisition circuitry 45.

The position sensors 31 to 33 may each be, for example, a magnetic sensor, an infrared sensor, or the like. As an exemplary case, when magnetic sensors are adopted, they detect magnetism from the transmitter and acquire the position signals based on the predetermined reference position. When infrared sensors are adopted, they detect infrared rays from the transmitter and acquire the position signals based on the predetermined reference position. Instead of such an infrared ray-utilizing technique, more general electromagnetic wave-utilizing technique may be adopted. Also, the reference position may be discretionarily adjusted according to, for example, operator's instructions input via the input interface 43.

The acquisition circuitry 45 is adapted to calculate positions of the respective position sensors 31 to 33, which may be expressed as (X1, Y1, Z1) to (X3, Y3, Z3) and which are based on the position of the transmitter, from the position signals acquired upon signal transmission and reception between the transmitter and each of the position sensors 31 to 33. This gives position information for the X-ray detector 16.

More specifically, the acquisition circuitry 45 uses the position signals output from the position sensors 31 to 33 to calculate the positions of the respective position sensors 31 to 33 based on the predetermined reference position. In one concrete implementation, the acquisition circuitry 45 acquires position information indicative of the position of the X-ray detector 16 in an absolute coordinate system defined with the predetermined reference position. The position sensors 31 to 33 and the acquisition circuitry together constitute one example of an acquirer for acquiring the position information for the X-ray detector 16.

The processing circuitry 44 with the determination function 444 obtains a positional relationship or positional relationships to the X-ray tube based on the acquired position information. For example, assuming that the X-ray tube is located at the origin (0, 0, 0), the X-ray detector 16 is determined to be in the state of substantially squarely facing toward the X-ray tube if distances D1 to D3 between the origin and the respective positions (X1, Y1, Z1) to (X3, Y3, Z3) of the position sensors 31 to 33 are approximately the same. Note that the distance D1 between the origin and the position (X1, Y1, Z1) of the position sensor 31 can be given as D1=(X1^2+Y1^2+Z1^2)^(½), where the symbol "^" indicates exponentiation. The distance D2 between the origin and the position (X2, Y2, Z2) of the position sensor 32, and the distance D3 between the origin and the position (X3, Y3, Z3) of the position sensor 33 are likewise obtained. The position of the X-ray tube can be acquired from the memory 41 via the system control function 441. The determination function 444 also determines the obtained positional relationships to be proper if such positional relationships indicate that the X-ray detector 16 is in the state of substantially squarely facing toward the X-ray tube. The processing circuitry 44 with the determination function 444 is one example of a processor and a determiner.

The remaining aspects are the same as the first embodiment.

Figure 18:
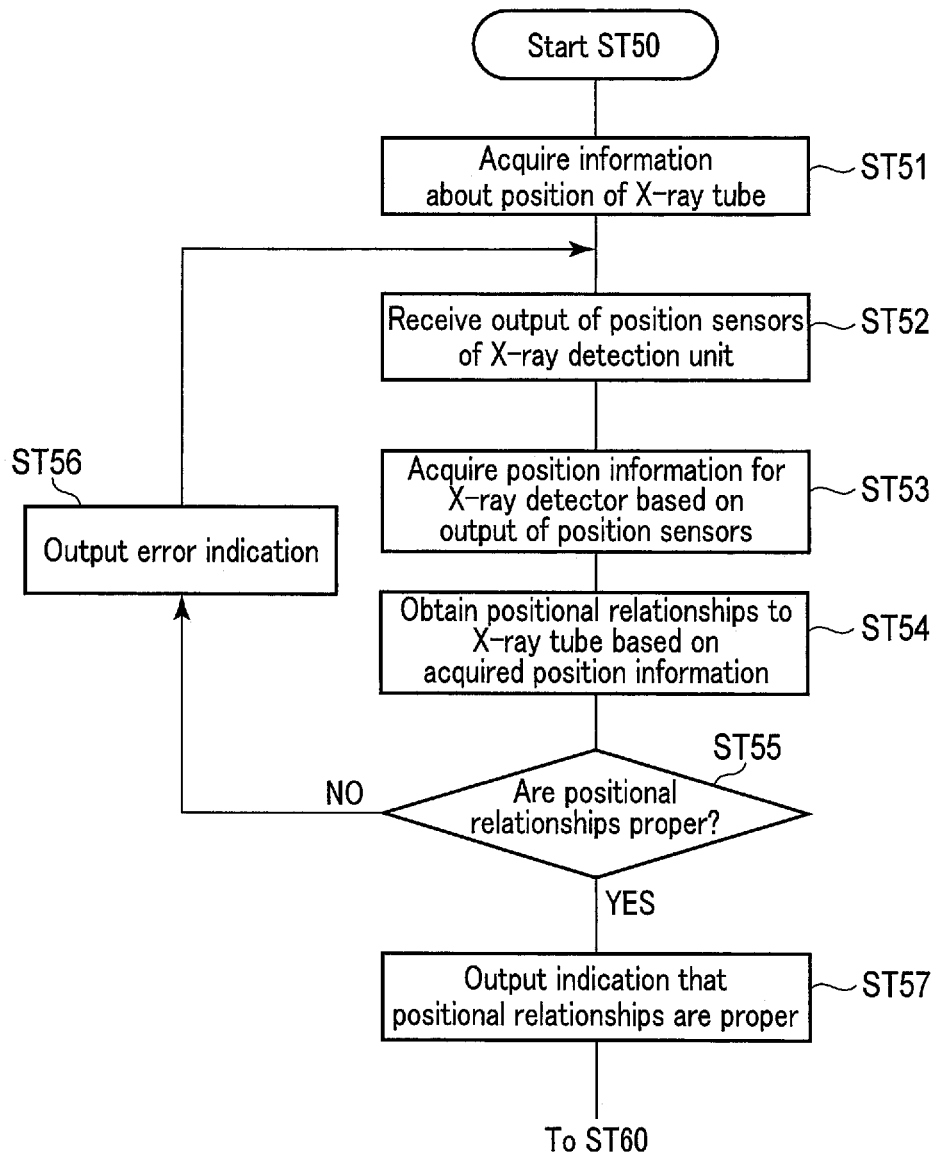
FIG. 18 is a flowchart for explaining one exemplary operation of the X-ray diagnostic apparatus according to the fifth embodiment.

Next, operations associated with the X-ray diagnostic apparatus with the above configuration according to this embodiment will be described with reference to the flowchart of FIG. 18. Note that the description will basically concentrate on operations corresponding to step ST50 (adjusting the imaging point for the subject P) as in the first embodiment.

It is supposed that steps ST10 to ST40 have now been performed in the manner as discussed, whereby the container 11 is placed in close contact with the subject P.

In step ST50 after step ST40, the imaging point for the subject P is adjusted while the close contact between the container 11 and the subject P is maintained. The concrete manner of adjusting the imaging point for the subject P may also include adjusting or changing the posture of the subject P seated in the wheelchair C20 by the operator, etc. Here, step ST50 according to this embodiment is performed as steps ST51 to ST57 as shown in FIG. 18.

In step ST51, the processing circuitry 44 acquires information about the position of the X-ray tube from the memory 41.

In step ST52 after step ST51, the position sensors 31 to 33 of the X-ray detection unit 10 output position signals for the X-ray detector 16. The acquisition circuitry 45 receives these position signals.

In step ST53 after step ST52, the acquisition circuitry 45 calculates the positions of the respective position sensors 31 to 33 based on a predetermined reference position, using the position signals output from the position sensors 31 to 33. More concretely, the acquisition circuitry 45 acquires position information indicative of the position of the X-ray detector 16 in an absolute coordinate system defined with the predetermined reference position.

In step ST54 after step ST53, the processing circuitry 44 obtains positional relationships to the X-ray tube based on the acquired position information. The positional relationships to obtain here may be, for example, the distances between the position of the X-ray tube and the respective positions of the position sensors 31 to 33. If the positional relationships indicate that the distances between the X-ray tube and the respective position sensors 31 to 33 are approximately the same, the X-ray detector 16 substantially squarely faces toward the X-ray tube.

In step ST55 after step ST54, the processing circuitry 44 determines whether the obtained positional relationships are proper or not. For example, in response to determining that the distances having been obtained as the positional relationships differ from each other in an amount equal to or larger than a reference value (ST55; NO), the processing circuitry 44 transitions to step ST56. On the other hand, in response to determining that the amount of differences between the distances are below the reference value, and therefore, the X-ray detector 16 substantially squarely faces toward the X-ray tube (ST55; YES), the processing circuitry 44 transitions to step ST57 as the positional relationships are determined to be proper.

When the operation flow proceeds to step ST56 after step ST55, the processing circuitry 44 outputs an error indication. The processing circuitry 44, for example, causes the display 42 to display an error message. The operation flow then returns to step ST52.

When, on the other hand, the operation flow proceeds to step ST57 after step ST55, the processing circuitry 44 outputs an indication that the positional relationships are proper. The processing circuitry 44, for example, causes the display 42 to display a message confirming that the positional relationships are proper. Step ST50 including steps ST51 to ST57 is thus complete.

After step ST50, step ST60 is performed in the similar manner as discussed.

According to the fifth embodiment as described above, the position information for the X-ray detector 16 is acquired, and the positional relationships to the X-ray tube are obtained based on the acquired position information. Also, upon obtaining the positional relationships, the obtained positional relationships are determined to be proper if they are indicative of the X-ray detector 16 being substantially squarely facing toward the X-ray tube. Accordingly, the fifth embodiment allows the X-ray imaging to be securely performed with the proper positional relationships, and therefore, it provides further advantages of improving the quality of X-ray images and avoiding a redo of the X-ray imaging so that an amount of exposure is reduced, in addition to the effects and advantages as in the first embodiment.

Note that the fifth embodiment is applicable to each of the second to the fourth embodiments. If indeed applied, the effects and advantages of the fifth embodiment will additionally be attained while the effects and advantages of the combined embodiment are enjoyed.

Sixth Embodiment

An x-ray diagnostic apparatus including an X-ray detection unit according to the sixth embodiment will be described with reference to FIGS. 19 and 20.

Figure 19:
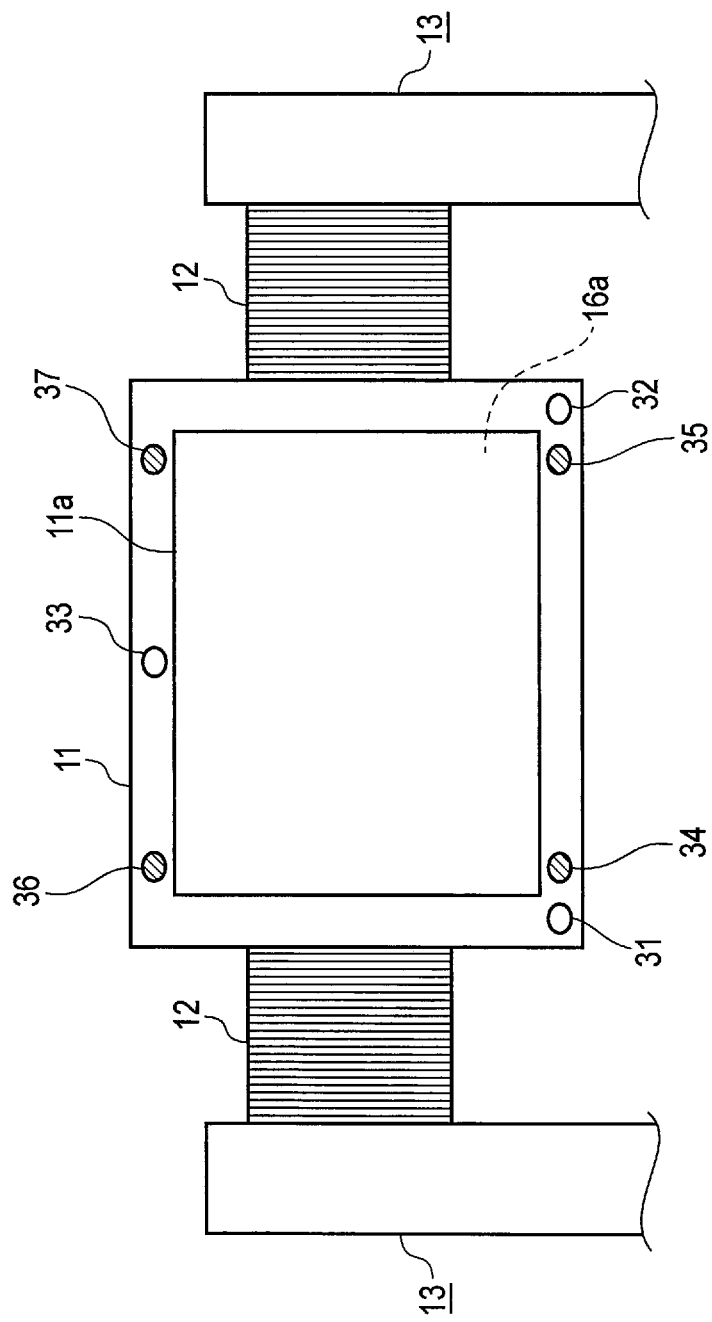
FIG. 19 is a front view of certain components of an X-ray detection unit according to a sixth embodiment.
Figure 20:
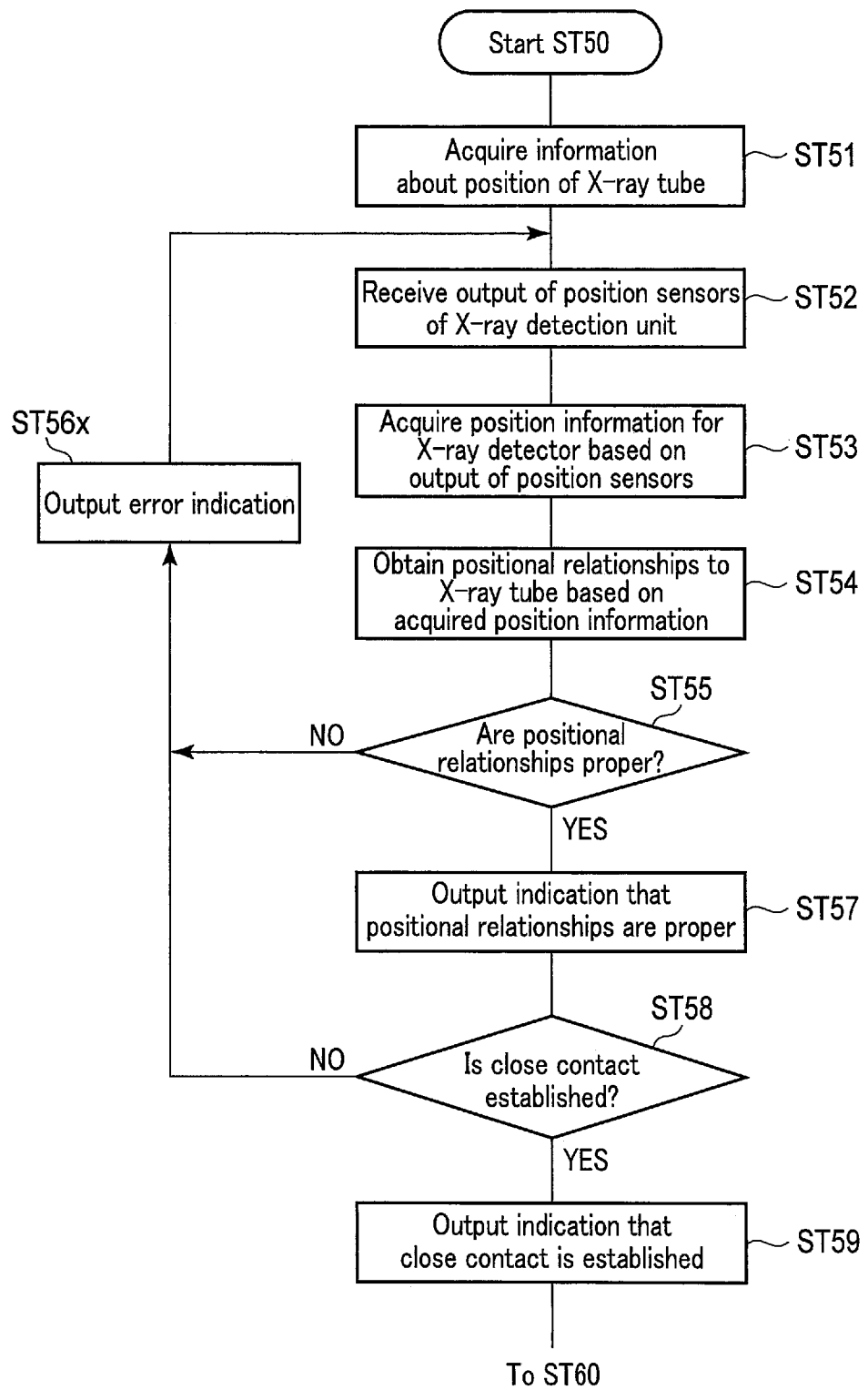
FIG. 20 is a flowchart for explaining one exemplary operation of the X-ray diagnostic apparatus according to the sixth embodiment.

The sixth embodiment may be understood as a modification of the fifth embodiment, and it additionally employs four close-contact sensors 34 to 37 near the above-described three position sensors 31 to 33 as shown in FIG. 19.

The close-contact sensors 34 to 37 are arranged at, for example, four respective corners of the peripheral portion of the area 11a of the container 11 that faces the detection plane 16a of the X-ray detector 16, and are each adapted to detect the subject P becoming in close contact with the container 11 and output detection signals. The close-contact sensors 34 to 37 may each be, for example, a piezoelectric sensor for converting pressure applied from the subject P into electric signals. The close-contact sensors 34 to 37 are however not limited to such components, and the examples of the close-contact sensors 34 to 37 also include switches adapted to output an on signal or an off signal in response to a pressing action by the subject P. The number and the arrangement of the close-contact sensors 34 to 37 here are only examples, and may be determined as appropriate. According to the embodiment, the processing circuitry 44 with the determination function 444 additionally determines whether or not the subject P is in close contact based on the output from the close-contact sensors 34 to 37. The close-contact sensors 34 to 37 (such as piezoelectric sensors, switches, etc.) each are an example of a pressure sensor provided at the container 11 of the X-ray detection unit 10 and adapted to detect the state of contact between the container 11 and the subject P. The determination function 444 of the processing circuitry 44 is one exemplary function of a processor, and it includes determining that the subject P is in contact with the container 11 based on the output of the pressure sensor.

The remaining aspects are the same as the fifth embodiment.

Next, operations associated with the X-ray diagnostic apparatus with the above configuration according to this embodiment will be described with reference to the flowchart of FIG. 20. Note that the description will basically concentrate on operations corresponding to step ST50 (adjusting the imaging point for the subject P) as in the fifth embodiment.

It is supposed that steps ST10 to ST40 have now been performed in the manner as discussed, whereby the container 11 is placed in close contact with the subject P.

In step ST50 after step ST40, the imaging point for the subject P is adjusted while the close contact between the container 11 and the subject P is maintained. The concrete manner of adjusting the imaging point for the subject P may also include adjusting or changing the posture of the subject P seated in the wheelchair C20 by the operator, etc. Here, step ST50 according to this embodiment is performed as steps ST51 to ST59 as shown in FIG. 20.

Steps ST51 to ST57 are performed in the manner as discussed.

Then, in step ST58 after step ST57, the processing circuitry 44 determines whether or not the subject P is in close contact with the container 11 based on the output from the close-contact sensors 34 to 37. If it is determined that the subject P is not in close contact with the container 11 (ST58; NO), the processing circuitry 44 transitions to step ST56x. On the other hand, if it is determined that the subject P is in close contact with the container 11 (ST58; YES), the processing circuitry 44 transitions to step ST59.

When the operation flow proceeds to step ST56x after step ST58, the processing circuitry 44 outputs an error indication. For example, the processing circuitry 44 causes the display 42 to display an error message. Note that such an error message used in step ST56x may indicate that the positional relationships are not proper if the result of determination in step ST55 is NO, and indicate that the close contact has not been established if the result of determination in step ST58 is NO. In any case, the operation flow returns to step ST52 after step ST56x.

When, on the other hand, the operation flow proceeds to step ST59 after step ST58, the processing circuitry 44 outputs an indication that the close contact has been established. The processing circuitry 44, for example, causes the display 42 to display a message confirming that the subject P is in close contact. Note that this message may instead indicate that everything has been set for imaging. In any case, step ST50 including steps ST51 to ST59 is complete upon finishing step ST59.

After step ST50, step ST60 is performed in the similar manner as discussed.

According to the sixth embodiment as described above, whether or not the subject P is in close contact with the container 11 is determined based on the output from the pressure sensors. For example, the state of close contact of the subject P is determined based on the output from the close-contact sensors 34 to 37. Accordingly, the sixth embodiment allows the X-ray imaging to be securely performed with the subject P being in the desired close contact state, and therefore, it provides further advantage of even enhancing the effects of improving the quality of X-ray images and avoiding a redo of the X-ray imaging so that an amount of exposure is reduced, in addition to the effects and advantages as in the fifth embodiment.

Note that the sixth embodiment is applicable to each of the second to the fourth embodiments. If indeed applied, the effects and advantages of the sixth embodiment will additionally be attained while the effects and advantages of the combined embodiment are enjoyed.

Seventh Embodiment

Figure 21:
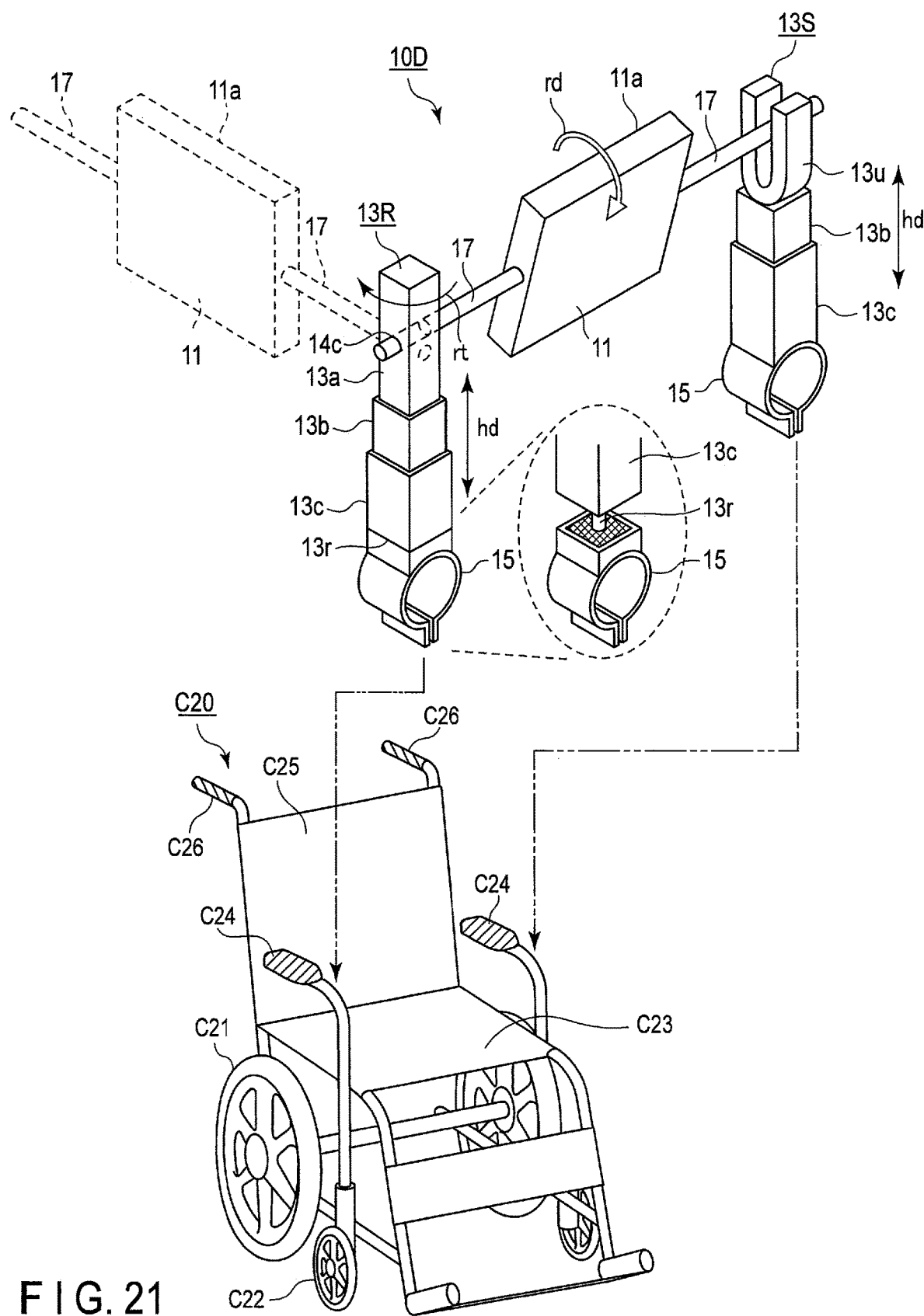
FIG. 21 is a perspective view of one exemplary design of an X-ray detection unit and a wheelchair according to a seventh embodiment.

An X-ray diagnostic apparatus according to the seventh embodiment will be described with reference to FIG. 21.

The seventh embodiment may be understood as a modification of the second embodiment, and its configuration enables X-ray imaging to be performed from the side of the subject P. The embodiment adopts an X-ray detection unit 10D which includes two column members 13S and 13R in place of the two column members 13's shown in FIG. 8. One of these column members 13S and 13R, namely, the column member 13S here, includes a support 13u in place of the first column piece 13a shown in FIG. 8, at the upper end of the second column piece 13b. The support 13u has, for example, an open-topped concave shape like a substantially "U" shape, and is adapted to support the rod member 17 in such a manner that the rod member 17 can be discretionarily detached and attached for placement. Note that the shape of the support 13u is not limited to the open-topped concave shape, but may instead be an open-sided concave shape like a substantially "C" shape, or any other shape. Also, the support 13u is not required to support the rod member 17 to be always detachable and attachable, but may lock the rod member 17 using a lid or the like that can close the concave shape. The other column member 13R includes a rotating mechanism 13r at the proximal end of the third column piece 13c, which enables rotational movement about the longitudinal axis of the column member 13R. The rotating mechanism 13r is provided between the third column piece 13c and the retentive part 15 and rotatably connect them together. The column member 13R is thus adapted to rotate in, for example, a circumferential direction rt with respect to the center axis. The rod member 17, the column member 13R, the rotating mechanism 13r, the through-holes 14c, and the retentive part 15 constitute yet another example of the attachment portion. As such, the attachment portion according to this embodiment includes a configuration that can move the container 11 between a position where the detection plane 16a faces the front face of the subject P and a position where the detection plane 16a faces the side face of the subject P. The position where the detection plane 16a faces the front face of the subject P may be regarded as a position where the longitudinal axis of the rod member 17 (before the rotational movement) and the rotational axis of the drive wheels C21's are substantially parallel to each other. The position where the detection plane 16a faces the side face of the subject P may be regarded as a position where the longitudinal axis of the rod member 17 (after the rotational movement) and the rotational axis of the drive wheels C21's are substantially orthogonal to each other. The configuration for moving the position of the container 11 is the rotating mechanism 13r for enabling the substantially horizontal rotation.

The remaining aspects are the same as the second embodiment.

With the above configuration, the same effects and advantages as in the second embodiment can be obtained by having the support 13u support the rod member 17. Additionally with this configuration, the rod member 17 is released by, for example, pressing down the support 13u of the column member 13S along the height direction hd, and then, the other column member 13R is rotated in the circumferential direction rt ("first rotation") so that the container 11 is brought into a state of facing the side face of the subject P. Note that, in the course of this first rotation, the rod member 17 is also rotated in the circumferential direction rd ("second rotation") by approximately 180° or a half rotation as needed so that the container 11 is turned upside down. This is because only the first rotation does not appropriately cause the detection plane 16a of the X-ray detector 16, which has been facing the subject P, to face the subject P after the rotational movement; that is, the first rotation alone causes only the backside of the detection plane 16a to face the subject P.

Therefore, the area 11a of the container 11 that faces the detection plane 16a is caused to face the side face of the subject P by conducting both the first rotation and the second rotation, and the X-ray imaging can be thereby performed from the side of the subject P seated in the wheelchair C20.

The seventh embodiment as described above provides the same effects and advantages as in the second embodiment, and additionally provides an advantage that X-ray imaging on the side face of the subject P is possible thanks to the configuration of having the rotatable column member 13R.

According to at least one embodiment as described above, the container contains the flat X-ray detector, and the attachment portion is coupled with the container and detachably mounted to a part of the wheelchair in which the subject is seated, so that the detection plane of the X-ray detector set in the container faces the subject. Thus, the at least one embodiment can eliminate the necessity of using a special, X-ray imaging-purpose wheelchair, and can also free a patient from the need of taking a difficult stance for X-ray imaging so that the burden on the patient is mitigated.

The term "processor" used herein refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (FPGA)), and so on. The processor reads programs stored in the memory and executes them to realize the respective functions. The programs may be incorporated directly in circuits of the processor, instead of being stored in the memory. According to such implementation, the processor reads the programs incorporated in its circuits and executes them to realize the functions. The embodiments, etc. do not limit the processor to a single circuitry-type processor. A plurality of independent circuits may be combined and integrated as one processor to realize the intended functions. Furthermore, multiple components or features as given in FIGS. 1 and 15 may be integrated as one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of

The invention claimed is:

1. An X-ray detection unit for a wheelchair, the X-ray detection unit comprising:
a flat X-ray detector;
a container configured to contain the X-ray detector; and
an attachment portion coupled with the container and configured to be detachably mounted to a part of the wheelchair in which a subject is seated, so that a detection plane of the X-ray detector in the container faces a front face of the subject seated in the wheelchair and an x-ray transmitted through the subject is detected by the X-ray detector.

2. The X-ray detection unit according to claim 1, wherein the attachment portion is attachable to a handle or an armrest of the wheelchair.

3. The X-ray detection unit according to claim 1, wherein the attachment portion comprises
a plurality of retentive parts configured to detachably retain respective handles or respective armrests of the wheelchair, and
a configuration for adjusting positions of the retentive parts in a width direction of the wheelchair.

4. The X-ray detection unit according to claim 3, wherein the configuration for adjusting the positions of the retentive parts in the width direction comprises
a coupling member connected to the container and having a longitudinal direction conforming to the width direction,
a slide support configured to support the coupling member so that the coupling member is slidable in the width direction, and
a column member provided with the slide support and respective one of the retentive parts, and having a longitudinal direction conforming to a height direction orthogonal to the width direction.

5. The X-ray detection unit according to claim 1, wherein the attachment portion comprises a configuration for adjusting a position of the container in a height direction of the wheelchair.

6. The X-ray detection unit according to claim 1, wherein the attachment portion comprises a configuration for moving the container between a position where the detection plane faces the front face of the subject and a position where the detection plane faces a side face of the subject.

7. The X-ray detection unit according to claim 6, wherein the configuration for moving the container is a rotating mechanism that enables a substantially horizontal rotation.

8. An X-ray diagnostic apparatus comprising:
the X-ray detection unit according to claim 1;
acquisition circuitry configured to acquire position information for the X-ray detector; and
processing circuitry configured to obtain a positional relationship to an X-ray tube based on the acquired position information.

9. The X-ray diagnostic apparatus according to claim 8, wherein the processing circuitry is configured to determine that the obtained positional relationship is proper if the positional relationship is indicative of the X-ray detector being substantially squarely facing toward the X-ray tube.

10. The X-ray diagnostic apparatus according to claim 8, further comprising a pressure sensor at the container of the X-ray detection unit, the pressure sensor configured to detect a state of contact between the container and the subject,
wherein the processing circuitry is configured to determine that the subject is in contact with the container based on an output of the pressure sensor.

11. An X-ray detection unit for a wheelchair, the X-ray detection unit comprising:
a flat X-ray detector;
a container configured to contain the X-ray detector; and
an attachment portion coupled with the container and configured to be detachably mounted to a part of the wheelchair in which a subject is seated, so that a detection plane of the X-ray detector in the container faces the subject,
wherein the attachment portion comprises a configuration for adjusting a position of the container in a height direction of the wheelchair, and the configuration for adjusting the position of the container in the height direction is a variable-length mechanism.

12. An X-ray detection unit for a wheelchair, the X-ray detection unit comprising:
   a flat X-ray detector;
   a container configured to contain the X-ray detector; and
   an attachment portion coupled with the container and configured to be detachably mounted to a part of the wheelchair in which a subject is seated, so that a detection plane of the X-ray detector in the container faces the subject,
   wherein the attachment portion comprises a configuration for adjusting a position of the container in a front-and-back direction of the wheelchair.

13. The X-ray detection unit according to claim 12, wherein the configuration for adjusting the position of the container in the front-and-back direction is a variable-length mechanism.

\* \* \* \* \*